US011857613B2

(12) United States Patent
Roland et al.

(10) Patent No.: US 11,857,613 B2
(45) Date of Patent: *Jan. 2, 2024

(54) VACCINE FOR PREVENTION OF NECROTIC ENTERITIS IN POULTRY

(71) Applicant: ARIZONA BOARD OF REGENTS ON BEHALF OF ARIZONA STATE UNIVERSITY, Scottsdale, AZ (US)

(72) Inventors: Kenneth Roland, Mesa, AZ (US); Andrew Diamos, Mesa, AZ (US); Hugh Mason, Phoenix, AZ (US)

(73) Assignee: ARIZONA BOARD OF REGENTS ON BEHALF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/089,056

(22) Filed: Dec. 27, 2022

(65) Prior Publication Data

US 2023/0142894 A1 May 11, 2023

Related U.S. Application Data

(62) Division of application No. 17/474,797, filed on Sep. 14, 2021, now Pat. No. 11,564,981, which is a division of application No. 16/628,860, filed as application No. PCT/US2018/040632 on Jul. 2, 2018, now Pat. No. 11,154,606.

(60) Provisional application No. 62/528,696, filed on Jul. 5, 2017.

(51) Int. Cl.
| | |
|---|---|
| *A61K 39/08* | (2006.01) |
| *A61P 31/04* | (2006.01) |
| *C12N 15/74* | (2006.01) |
| *C12N 15/82* | (2006.01) |
| *A61K 39/00* | (2006.01) |

(52) U.S. Cl.
CPC .............. *A61K 39/08* (2013.01); *A61P 31/04* (2018.01); *C12N 15/74* (2013.01); *C12N 15/8258* (2013.01); *A61K 2039/552* (2013.01); *A61K 2039/55577* (2013.01)

(58) Field of Classification Search
None
See application file for complete search history.

*Primary Examiner* — Oluwatosin A Ogunbiyi
(74) *Attorney, Agent, or Firm* — Viksnins Harris Padys Malen LLP

(57) ABSTRACT

In certain embodiments, the present invention provides a poultry vaccine comprising an antigenic protein comprising a PlcC protein unit that is operably linked to a peptide linker that is operably linked to a NetB protein unit, where the vaccine is effective in stimulating a protective cellular and/or humoral immune response to *C. perfringens*. Methods are also provided for making the vaccine and for vaccinating poultry by administering such a vaccine.

8 Claims, 6 Drawing Sheets

Specification includes a Sequence Listing.

Figure 2

VACCINE FOR PREVENTION OF NECROTIC ENTERITIS IN POULTRY

CROSS-REFERENCE TO RELATED APPLICATIONS

This application is a divisional application of U.S. patent application Ser. No. 17/474,797, filed Sep. 14, 2021, now U.S. Pat. No. 11,564,981, issued Jan. 31, 2023, which application is a divisional application of U.S. patent application Ser. No. 16/628,860, filed Jan. 6, 2020, now U.S. Pat. No. 11,154,606, issued Oct. 26, 2021, which claims priority to International Application Number PCT/US2018/040632, filed Jul. 2, 2018, which claims the benefit of priority of U.S. Provisional Application Ser. No. 62/528,696, filed Jul. 5, 2017. The entire content of the applications referenced above is hereby incorporated by reference herein.

SEQUENCE LISTING

The instant application contains a Sequence Listing which has been submitted in XML format via Patent Center and is hereby incorporated by reference in its entirety. Said XML copy, created on Dec. 26, 2022, is named 17555051US3.xml and is 43,871 Bytes in size.

BACKGROUND

*C. perfringens* is a ubiquitous gram positive, spore-forming, anaerobic organism, found in many environments surrounding poultry production, including soil, dust, feces, feed, litter, rodents, and the intestinal contents of asymptomatic animals. *C. perfringens* is classified into five groups based on the types of toxins secreted, but only *C. perfringens* type A strains are commonly associated with enteric disease in poultry. The toxins produced by type A *C. perfringens* strains cause necrotic enteritis (NE) in colonized birds. Severe acute cases can result in sudden death, while subclinical necrotic enteritis results in thickening of the intestinal mucosa and decreased length of microvilli in the ileum. The collective impact of *C. perfringens* colonization is to reduce the absorptive surface in the intestinal tract with a consequent reduction in the ability of birds to benefit from nutrients in food, resulting in a reduced rate of growth. *C. perfringens* also induces cellulitis and gangrenous dermatitis and is becoming an increasing concern in turkeys as well.

This application claims the benefit of priority of U.S. Provisional Application Ser. No. 62/528,696, filed Jul. 5, 2017, which application is incorporated by reference herein.

*C. perfringens* infections and NE have been traditionally controlled by addition of Antimicrobial Growth Promoters (AGP) and coccidiostats in the animal feed. Large quantities of antimicrobials were used as AGP and as prophylaxis against enteric bacterial pathogens, including *C. perfringens*. The use of AGP has been condemned due to concerns about increased antibiotic resistance in human pathogens. Consequently, an increase in the incidence of sub-clinical NE is linked to the withdrawal of AGP. This had been observed initially in Scandinavian countries following the ban on AGP in the early 1990s. Furthermore, the decline in use of ionophore coccidiostats, which can prevent *C. perfringens* lesions, has exacerbated the resurgence of NE. Recent moves by the US congress and the FDA to restrict the use of growth promoting antibiotics and public pledges by major poultry consumers (e.g. McDonald's, Costco, Chick-fil-A) to eliminate antibiotic-fed poultry from their menus, indicates that the old practices are on the way out. Thus, NE is a re-emerging disease and a threat to the current objective of "antimicrobial-free" poultry farming.

Most birds infected with virulent strains remain asymptomatic and show reduced growth performance. *C. perfringens* can cause a range of health problems in infected birds, ranging from a subclinical infection which can result in poor feed conversion caused by decreased digestion and adsorption, to necrotic enteritis, resulting in a variety of symptoms including severe depression, decreased appetite, reluctance to move, diarrhea and ruffled feathers, often leading to death. Clinical illness is usually short, with birds often simply found dead. Onset of disease symptoms generally occurs in broilers from two to five weeks of age, coinciding with the disappearance of maternal antibodies. However, NE has also been reported in layers of various ages. Gross lesions typically involve the duodenum, jejunum and sometimes the ileum, although even cecal lesions can occur. Intestines are friable and distended with gas and fluid and a diphtheritic membrane is often found in the mucosa. Subclinical infection with *C. perfringens* can lead to economic losses, due to reduced growth rates and poor feed conversion. It is likely that losses due to subclinical infections may constitute a larger problem overall than losses due to acute disease. Occasionally, cholangiohepatitis can result, leading to condemnation losses.

Diet has also been implicated as a factor that can predispose birds to NE. Inclusion of wheat, rye, barley, oat groats or fish meal in the diet can lead to increased numbers of *C. perfringens* and incidence of NE. Dietary fat source can also influence the *C. perfringens* population (19). Current thinking is that predisposing factors such as a high protein diet (e.g. fishmeal) and/or *Eimeria* infection result in alterations of the chicken gut microbiota that allow incoming pathogenic *C. perfringens* strains to become established.

Thus, there is an unmet need for an improved, effective vaccine against *C. perfringens* that protects the birds against the disease. A vaccine that would protective immunity would meet this need.

SUMMARY

Necrotic enteritis caused by *Clostridium perfringens* is a serious economic problem in the broiler industry, with losses up to $2 billion annually. In the US, this problem is likely to be exacerbated as the use of antibiotics in poultry rearing is phased out. This invention describes a method to produce in plants, a novel protein fusing two toxoids that elicit immune responses protective against necrotic enteritis. The fusion protein antigen can be purified from plant cells for use as an injectable vaccine or can by directly applied to poultry feed for use as an oral vaccine.

In certain embodiments, the present invention provides an antigenic protein comprising a PlcC protein unit that is operably linked to a peptide linker that is operably linked to a NetB protein unit.

In certain embodiments, the present invention provides a nucleic acid encoding the antigenic protein described herein.

In certain embodiments, the present invention provides an expression cassette comprising the nucleic acid described herein and a promoter.

In certain embodiments, the present invention provides a recombinant vector comprising the expression cassette described herein and a vector.

In certain embodiments, the present invention provides a plant cell comprising the antigenic protein described herein, the nucleic acid described herein, the expression cassette described herein or the recombinant vector described herein.

In certain embodiments, the present invention provides animal feed comprising the plant cell described herein.

In certain embodiments, the present invention provides a vaccine comprising the antigenic protein described herein, the nucleic acid described herein, the expression cassette described herein, the recombinant vector described herein, the plant cell described herein, or the animal feed described herein.

In certain embodiments, the present invention provides a method of protecting an avian species from *C. perfringens* infections comprising administering the vaccine described herein.

BRIEF DESCRIPTION OF DRAWINGS

FIG. 2. Schematic of PlcC-NetB fusion protein.

FIG. 4A. PlcC0NetB titers; FIG. 4B. PlcC titers; FIG. 4C. NetB titers. * P≤0.009.

DETAILED DESCRIPTION

Figure 1:
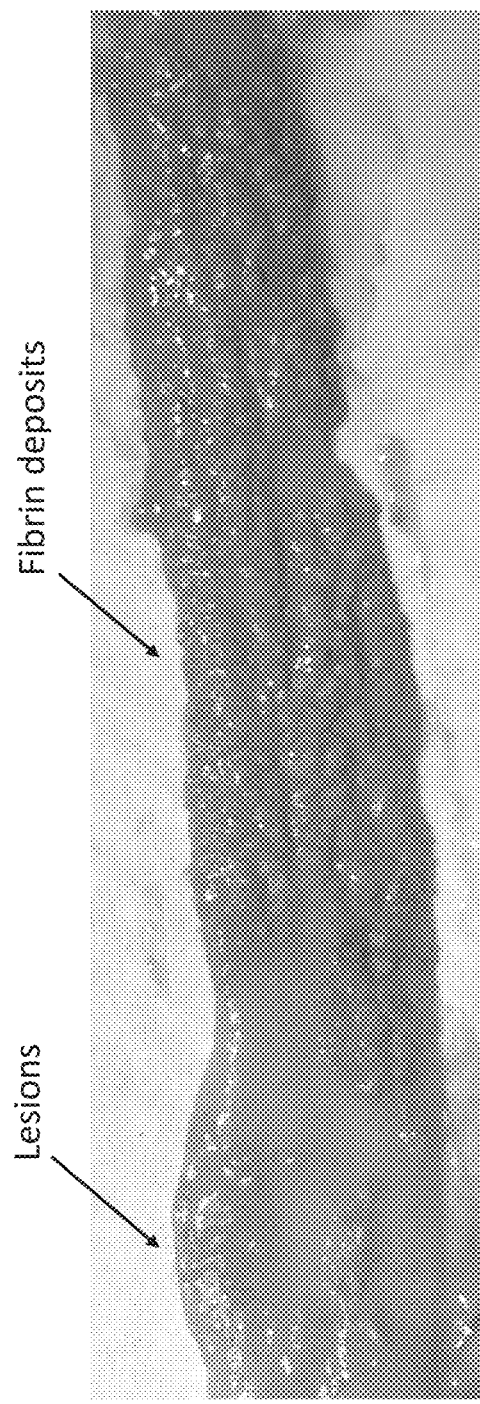
FIG. 1. Fibrin deposits and lesions on the intestinal tract of a chicken with necrotic enteritis.

Necrotic enteritis (NE) is caused by type A strains of the bacterium *Clostridium perfringens*. The total global economic losses to the poultry industry due to NE is estimated to be over 2 billion dollars annually. *C. perfringens* produces two toxins, alpha-toxin and NetB. The NetB toxin is responsible for the symptoms associated with NE and anti-NetB antibodies are protective. Immune responses against alpha-toxin are partially protective despite the fact that it does not play a direct role in NE. We describe a single fusion protein combining immunogenic and non-toxic components of alpha-toxin and NetB that can be used to immunize poultry against NE. The fusion protein is produced in plants which can be purified and used as an injectable preparation or fed directly to poultry to elicit a protective immune response.

The use of plants for the production and oral delivery of a necrotic enteritis vaccine is novel. Moreover, the PlcC-NetB fusion protein described here is novel and is strongly expressed in plants, which lack cholesterol and thus may be immune to the toxic effects of NetB, thus permitting the observed high expression level.

This novel fusion protein combines the two most potent protective antigens against necrotic enteritis, NetB and alpha-toxin, into a single antigenic protein. NetB is the toxin responsible for necrotic enteritis symptoms. The alpha-toxin (Plc) may also contribute to disease, and, in addition, antibodies against alpha-toxin are targeted to the surface of *C. perfringens*, inhibiting its growth. However, strains lacking alpha-toxin can cause disease, such that a vaccine relying only on immune responses against alpha-toxin will not provide protection against these strains. Combining both alpha-toxin and NetB epitopes will provide robust protection against disease. The PlcC-NetB protein can be purified from plants, in either a glycosylated or non-glycosylated form, and used as an injectable vaccine to protect birds directly. Injection into hens will protect their offspring in the first two weeks of life via maternal antibodies passed on in the egg. When this protein is produced in a food plant, such as corn, with or without an LT adjuvant, the resulting recombinant plant can be applied directly to the feed, resulting in a potentially low cost, oral vaccine to protect chickens against necrotic enteritis.

The use of plants for the production and oral delivery of a necrotic enteritis vaccine is novel. Moreover, the PlcC-NetB fusion protein described here is novel and is strongly expressed in plants, which lack cholesterol and thus may be immune to the toxic effects of NetB, thus permitting the observed high expression level.

*C. perfringens* type A strains produce alpha-toxin, a membrane-damaging phospholipase C enzyme. The toxin is hemolytic, necrotizing and lethal. It is the toxin that responsible for *C. perfringens*-mediated gas gangrene. Many of the symptoms of NE can be reproduced with culture-free supernatants of *C. perfringens*. Since these supernatants were known to contain alpha-toxin, it was assumed that alpha-toxin was responsible. More recent studies have identified a novel toxin linked to necrotic enteritis, designated NetB toxin. It was first identified in a virulent *C. perfringens* type A strain isolated in Australia and it has been detected in the vast majority of NE-associated *C. perfringens* strains throughout the world. Thus, it is now considered to be the most critical virulence factor for the development of NE in broilers. NetB is a pore-forming toxin encoded on a large conjugative plasmid (approximately 85 kb) within a 42 kilobase (kb) pathogenicity locus (NELoc-1), showing similarity to *C. perfringens* β-toxin (38% identity). The presence of netB gene is highly correlated with necrotic enteritis strains. NetB is also a protective antigen, particularly in combination with other immunogenic components. One study showed that the levels of serum antibodies against both alpha-toxin and NetB toxin were significantly higher in apparently healthy chickens compared to birds with clinical signs of NE, suggesting that these antitoxin antibodies play a role in protection. The large clostridial cytotoxin TpeL (predicted molecular mass=191 kDa), first identified in type C strains, is also produced by some type A strains and has been linked to increased virulence, particularly in strains producing netB. However, it should be noted that a recent study of historical NE strains collected >15 years ago in Alabama revealed a low prevalence of the netB gene, indicating that netB may be dispensable for some NE for some strains or in some situations. Nevertheless, it is clear that the overwhelming majority of current necrotic enteritis strains produce this toxin.

Toxins have traditionally been targeted as antigens of interest for controlling clostridial infections. The *C. perfringens* alpha-toxin (Plc) is the major virulence determinant for gas gangrene and antibodies to *C. perfringens* alpha-toxin prevent gas gangrene in mice. The *C. perfringens* gene encoding alpha-toxin is plc (for phospholipase C). The protein is divided into two domains, the amino-terminal domain encodes the catalytic site responsible for phospholipase activity, while the carboxy-terminal domain is involved in interactions with phospholipids, targeting the enzyme to host cell membranes. The alpha-toxin carboxy-terminal fragment (amino acids 247-370) is non-toxic and immunization with this fragment confers protection against alpha-toxin and *C. perfringens* in a gas gangrene mouse model. Immune responses against the C-terminal domain, PlcC, can provide protection against subsequent challenge with *C. perfringens*.

NetB binds to cholesterol in membranes, forming heptameric pores. A number of single amino acid substitutions in the rim loop region can significantly reduce its ability to bind to cells and its toxicity. These include Y191A, R200A, W257A and W262A, S254L, R230Q and W287R. Some of these were shown to retain the ability to generate protective immune responses, including W262A and S254L. A number of studies have demonstrated the potential of vaccination to control NE. A vaccine utilizing detoxified alpha-toxin can induce some protection against experimental infection. Since alpha-toxin is not required in order for *C. perfringens* to cause NE in chickens, it is not clear why alpha-toxoids are protective. One likely explanation is based on data showing that anti-alpha-toxin (anti-Plc) antibodies bind to the surface of Plc+ *C. perfringens* strains and that these antibodies can also inhibit *C. perfringens* growth. Thus, it is possible that the reason anti-Plc antibodies are protective is due to their growth inhibitory properties and not directly due to detoxification.

NetB is also a protective antigen, which could provide significant protection against NE challenge, especially in combination with other immunogenic components. Both alpha-toxin (C-fragment) and NetB (W262A) toxoids were combined (30 g of each) in Quil A adjuvant and used to subcutaneously inject broiler birds 3 times, on days 3, 9 and 15. Birds injected with only one of the proteins were also included. The immunized birds were partially protected against a mild challenge (gavage only), but not against a more severe, in feed challenge. In some studies, hens were infected with NetB toxoid and antibodies against NetB were transferred from immunized hens to their progeny, providing protection to the chicks against *C. perfringens* challenge. In another study, immunization with both NetB and alpha-toxin toxoids using a live *Salmonella* delivery vector induced mucosal antibodies against both toxins and elicited a protective response. *S. Typhimurium* vaccine trains engineered to deliver both toxoids provided significantly better protection than strains delivering each toxin alone.

Recently an injectable alpha-toxoid preparation produced by Intervet, called Netvax, has come on the market for use in broiler breeders to increase protection in chicks during the first few weeks of life. However, there is no commercial vaccine that includes a NetB immunogenic component. Several vaccine antigens have been stably expressed in corn and rice, which are convenient for use in feed products. Despite concerns regarding oral tolerance, feeding animals plant-based vaccines has been shown to be effective in agricultural animals, including poultry.

Proteins

In certain embodiments, the present invention provides an antigenic protein comprising a PlcC protein unit that is operably linked to a peptide linker that is operably linked to a NetB protein unit.

In certain embodiments, the PlcC protein unit, the peptide linker and the NetB protein unit each have an N-terminus and a C-terminus, and wherein the C-terminus of the PlcC protein unit is linked to the N-terminus of the peptide linker, and the C-terminus of the peptide linker is operably linked to the N-terminus of the NetB protein unit.

In certain embodiments, the PlcC protein unit has at least 95% sequence identity to SEQ ID NO: 3. The PlcC protein unit of SEQ ID NO: 3 is amino acids 248-370 of alpha toxin (GenBank accession AAP-15462.1).

In certain embodiments, the PlcC protein unit has 100% sequence identity to SEQ ID NO: 3.

In certain embodiments, the NetB protein unit has at least 95% sequence identity to SEQ ID NO: 5. The NetB protein unit of SEQ ID NO: 5 is amino acids 31-322 of (GenBank accession ACN73257.1).

In certain embodiments, the NetB protein unit has one or more amino acid substitutions at Y191A, R200A, W257A and W262A, S254L, R230Q or W287R of SEQ ID NO: 5.

In certain embodiments, the NetB protein unit has 100% sequence identity to SEQ ID NO: 5.

In certain embodiments, the peptide linker has at least 95% sequence identity to SEQ ID NO: 4.

In certain embodiments, the peptide linker has 100% sequence identity to SEQ ID NO: 4.

In certain embodiments, the antigenic protein further comprises a 6Hist tag having an N-terminus and a C-terminus, wherein the C-terminus of the 6Hist tag is operably linked to the N-terminus of the PlcC protein unit.

In certain embodiments, the 6His tag has 100% identity to SEQ ID NO: 2.

In certain embodiments, the antigenic protein further comprises a plant signal peptide having an N-terminus and a C-terminus, wherein the C-terminus of the plant signal peptide is operably linked to the N-terminus of the 6Hist tag.

In certain embodiments, the plant signal peptide has at least 95% sequence identity to SEQ ID NO: 1.

In certain embodiments, the plant signal peptide has 100% sequence identity to SEQ ID NO: 1.

The term "amino acid" includes the residues of the natural amino acids (e.g., Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g., phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes peptides with reduced peptide bonds, which will prevent proteolytic degradation of the peptide. Also, the term includes the amino acid analog α-amino-isobutyric acid. The term also includes natural and unnatural amino acids bearing a conventional amino protecting group (e.g., acetyl or benzyloxycarbonyl), as well as natural and unnatural amino acids protected at the carboxy terminus (e.g., as a ($C_1$-$C_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

A "variant" of one of the proteins that one that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Aline is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 80%, at least about 90%, or even at least about 91%, 92%, 93%, 94%, 95%, 96%, 97%, 98%, 99%, but less than 100%, contiguous amino acid sequence homology or identity to the amino acid sequence of a corresponding native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The terms "protein," "peptide" and "polypeptide" are used interchangeably herein.

Amino acid sequence of 6H-plcC-netB fusion protein:

(SEQ ID NO: 13)
mankhlslslflvllglsaslasg*HHHHHHgs*DPSVGNNVKELVAYISTS

GEKDAGTDDYMYFGIKTKDGKTQEWEMDNPGNDFMAGSKDTYTFKLKDEN

LKIDDIQNMWIRKRKYTAFPDAYKPENIKVIANGKVVVDKDINEWISGNS

TYNIK*ggsggsggpsggsggs*ELNDINKIELKNLSGEIIKENGKEAIKYT

SSDTASHKGWKATLSGTFIEDPHSDKKTALLNLEGFIPSDKQIFGSKYYG

KMKWPETYRINVKSADVNNNIKIANSIPKNTIDKKDVSNSIGYSIGGNIS

VEGKTAGAGINASYNVQNTISYEQPDFRTIQRKDDANLASWDIKFVETKD

GYNIDSYHAIYGNQLFMKSRLYNNGDKNFTDDRDLSTLISGGFSPNMALA

LTAPKNAKESVIIVEYQRFDNDYILNWETTQ<u>A</u>RGTNKLSSTSEYNEFMFK

INWQDHKIEYYL

Coding of Regions:
Lower case, regular type=ER signal peptide from barley alpha amylase gene
Upper case, Italics=6-His metal affinity tag
Lower case, italics=linker sequences
Upper case, regular type=plcC
Upper case, Bold type=netB (W262A mutation underlined)

In certain embodiments, e.g., for cytosolic instead of ER targeting, the N-terminal signal peptide (Lower case, regular type) is omitted.

Nucleic Acid

In certain embodiments, the present invention provides a nucleic acid encoding the antigenic protein described herein.

In certain embodiments, the nucleic acid has been plant-codon optimized for plant expression.

In certain embodiments, the nucleic acid has been plant-codon optimized for expression in *Nicotiana benthamiana* or *Arabidopsis*.

In certain embodiments, the nucleic acid has at least 95% sequence identity to SEQ ID NO: 6.

In certain embodiments, the nucleic acid has 100% sequence identity to SEQ ID NO: 6.

The fusion protein gene for the 6H-plcC-netB fusion protein (SEQ ID NO: 13 (amino acid sequence)) was codon optimized for expression in *Nicotiana benthamiana*. Each codon was assessed for its preference of use in highly expressed genes of *N. benthamiana*, *N. tabacum*, and *Arabidopsis thaliana*, using coding sequences obtained from Genbank accessions (Geyer, B. C., Kannan, L., Cherni, I., Woods, R. R., Soreq, H., and Mor, T. S. (2010) Transgenic plants as a source for the bioscavenging enzyme, human butyrylcholinesterase. Plant Biotechnol J. 8(8):873-86). Use of a particular codon was avoided if it represented less than 50% of the frequency of the most preferred synonymous codon in the reference gene set. The remaining codons were used at frequencies proportional to their frequencies of use in the reference gene set. Furthermore, A-rich sequences that could function as a polyadenylation near-upstream element were avoided, including AATAAA, AATGGA, AATGAA, TATAAA, AATAAT, AATAAG, AATATT, GATAAA, AACCAA, ATATAA, AATCAA, ATACTA, ATAAAA, ATGAAA, AAGCAT, ATTAAT, ATACAT, AAAATA, ATTAAA, AATTAA, AATACA, CATAAA, ACTAAA, and AAAAAA. Sequences that could function as 5' intron splice recognition sequences were avoided, including GTAACA, GTGCTC, GTTAGT, GTAAAT, GTAAAG, GTCTGT, GTAAGG, GTGAGT, GTAAAA, GTAAGT, GTAAGC, GTACGT, GTAACT, GTAAGA, GTTAAA, GTAATA, and GTACAT. As much as possible, sequences that could function as 3' intron splice recognition sequences were avoided, including GCAGG, CCAGG, TCAGG, ATAGG, GTAGG, TTAGG, ACAGG, and AAAGG. Potential RNA destabilizing sequences were avoided, including ATTTA, TAGATY, ATAGAT, and TTTTTT. Potential termination signals for RNA polymerase II were avoided as much as possible, including CA(N7-9)AGTNNA. The potential DNA C-methylation signal CCGG was avoided as much as possible.

Figure 6:
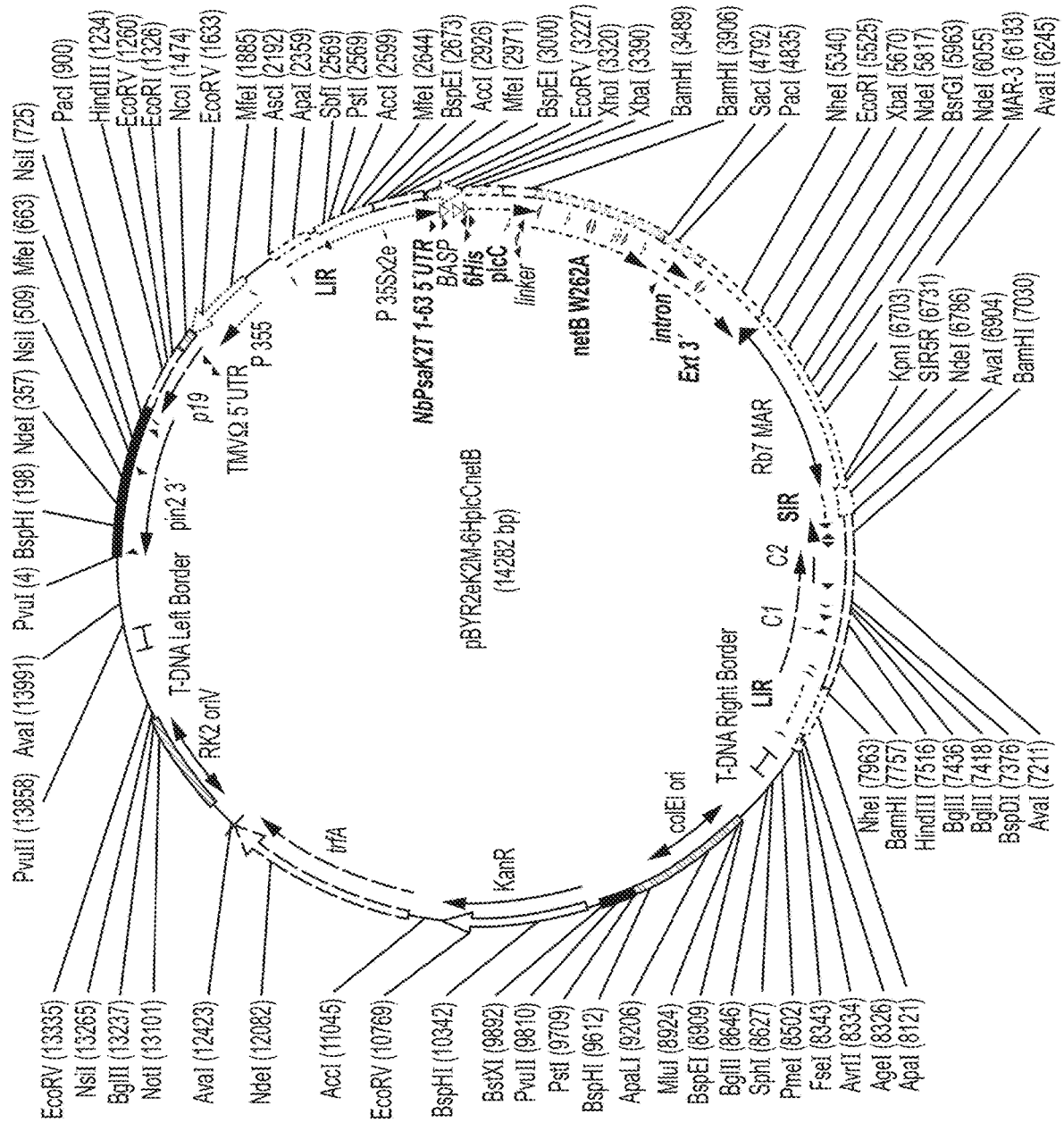
FIG. 6. Map of pBYR2eK2M-6HplcCnetB.

The nucleotide sequence of pBYR2eK2M-6HplcCnetB is the following (FIG. 6):

(SEQ ID NO: 14)

```
CGATCGGTCGATTCATAGAAGATTAGATTTTTCATAGTATTTTTTTAAAGTAAACCT

TTAACTACGGTTAGGAGACTTTTAAGTTAAATTTAATTTGAACCCTTAAATTAATTTTTAAA

ATAGATAAATATCAATCATCCTGATATGCTTTTGAAAAAATGAATGAGAAAGATGATTCAAT

TAAGGCCACATTTTAATCATGACTAAAATAATATACAGTATAATTTCATATATATTTGCTTT

AAAAAAAAATTGACAATCCATTCGTTTCTAGCAATAAATTTCTTCAACCACAAATATATTAA

AGATAACTACGGCATAGAAACAAAAATCTATGAAGAATTTTTGTATACTTCATATGAAATTA

AAAAAAACTTCATTGAACATCAAAATAATAATAATAATCATAAACTCCTCAATATTTATATT

CCTAGCTTCTTGAATTAAATTGTTTACATATTCAACGATGTAAAAAATTATTTCTCTATCTA

TTTTCCTTATATCATGCATGGTTTCACATATATCAAAGGATAAAAGCAATCTATGTAAATTA

TCTCACTTTATTAAGTTTTCTATCTGAATTATTGAGAACGTAGATTTCTTTTTGCACTATCC

CCCAATAATTAGCAAAACACACCTAGACTAGATTTGTTTTGCTAACCCAATTGATATTAATT

ATATATGATTAATATTTATATGTATATGGAATTGGTTAATAAAATGCATCTGGTTCATCAAA

GAATTATAAAGACACGTGACATTCATTTAGGATAAGAAATATGGATGATCTCTTTCTCTTAT

TCAGATAATTAGTAATTAGACATAACACACAACTTTGATGCCCACATTATAGTGATTAGCAT

GTCACTATGTGTGCATCCTTTTATTTCATACATTAATTAACTTGGCCAATCCAGAAGATGGA

CAAGTCTAGGGTCACATTGCAGGGTACTCTAGCTTACTCGCCTTCTTTTTCGAAGGTTTGAG

TACCTTCAGGGCATCCTCTTGATACATTACTTTCCACTTCGATTGGGGCAAGCTGTAGCAGT

TCTTGCTTAGACCGAATTGCCATCTCACAGAGATGCTGAAGAGTTCGCGACCCTCCAGAAAC

GGTGATACTAACTCCTCGAAACCGAATACTATAGGTACATCCGATCTGGTCGAAACCGAAAA

ATCGAGATGCTGCATAGTTAACCGAATCTCCCGTCCAAGATCCAAGGACTCTGTGCAGTGAA

GCTTCCGTCCTGTCGTATCTGAGATATCTCTTAAATACAACTTTCCCGAAACCCCAGCTTTC

CTTGAAACCAAGGGGATTATCTTGATTCGAATTCGTCTCATCGTTATGTAGCCGCCACTCAG

TCCAACTCGGACTTTCGTCAGGAAGTTTGAAGGGAGAAGTTGTACCTCCTGATCCTCCATCC

CAACGTTCACTGTTAGCTTGTTCCCTAGCGTCGTTTCCTTGTATAGCTCGTTCCATGGATTG

TAAATAGTAATTGTAATGTTGTTTGTTGTTTGTTGTTGTTGGTAATTGTTGTAAAAATACGC

TCTCCAAATGAAATGAACTTCCTTATATAGAGGAAGGGTCTTGCGAAGGATAGTGGGATTGT

GCGTCATCCCTTACGTCAGTGGAGATATCACATCAATCCACTTGCTTTGAAGACGTGGTTGG

AACGTCTTCTTTTTCCACGATGCTCCTCGTGGGTGGGGGTCCATCTTTGGGACCACTGTCGG

CAGAGGCATCTTCAACGATGGCCTTTCCTTTATCGCAATGATGGCATTTGTAGGAGCCACCT

TCCTTTTCCACTATCTTCACAATAAAGTGACAGATAGCTGGGCAATGGAATCCGAGGAGGTT

TCCGGATATTACCCTTTGTTGAAAAGTCTCAATTGCCCTTTGGTCTTCTGAGACTGTATCTT

TGATATTTTTGGAGTAGACAAGTGTGTCGTGCTCCACCATGTTCTGGCAATTCCGGTTCGCT

TGCTGTCCATAAAACCGCCCAGTCTAGCTATCGCCATGTAAGCCCACTGCAAGCTACCTGCT

TTCTCTTTGCGCTTGCGTTTTCCCTTGTCCAGATAGCCCAGTAGCTGACATTCATCCGGGGT

CAGCACCGTTTCTGCGGACTGGCTTTCTACGTGTTCCGCTTCCTTTAGCAGCCCTTGCGCCC

TGAGTGCTTGCGGCAGCGTGAAGCTGGCGCGCCGCTCTAGCAGAAGGCATGTTGTTGTGACT
```

-continued

```
CCGAGGGGTTGCCTCAAACTCTATCTTATAACCGGCGTGGAGGCATGGAGGCAAGGGCATTT
TGGTAATTTAAGTAGTTAGTGGAAAATGACGTCATTTACTTAAAGACGAAGTCTTGCGACAA
GGGGGGCCCACGCCGAATTTTAATATTACCGGCGTGGCCCCACCTTATCGCGAGTGCTTTAG
CACGAGCGGTCCAGATTTAAAGTAGAAAAGTTCCCGCCCACTAGGGTTAAAGGTGTTCACAC
TATAAAAGCATATACGATGTGATGGTATTTGATAAAGCGTATATTGTATGAGGTATTTCCGT
CGGATACGAATTATTCGTACGACCCTCCTGCAGGTCAACATGGTGGAGCACGACACACTTGT
CTAGTCCAAAAATATCAAAGATACAGTCTCAGAAGACCAAAGGGCAATTGAGACTTTTCAAC
AAAGGGTAATATCCGGAAACCTCCTCGGATTCCATTGCCCAGCTATCTGTCACTTTATTGTG
AAGATAGTGGAAAAGGAAGGTGGCTCCTACAAATGCCATCATTGCGATAAAGGAAAGGCCAT
CGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATAACATGGTG
GAGCACGACACACTTGTCTACTCCAAAAATATCAAAGATACAGTCTCAGAAGACCAAAGGGC
AATTGAGACTTTTCAACAAAGGGTAATATCCGGAAACCTCCTCGGATTCCATTGCCCAGCTA
TCTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCCCC
ACCCACGAGGAGCATCGTGGAAAAGAAGACGTTCCAACCACGTCTTCAAAGCAAGTGGATT
GATGTGATATCTCCACTGACGTAAGGGATGACGCACAATCCCACTATCCTTCGCAAGACCCT
TCCTCTATATAAGGAAGTTCATTTCATTTGGAGAGGACCTCGAGAAACAAACAAAATCAACA
AATATAGAAAATAACGCATTTCCAATTCTTTGAAATTTCTGCAACATCTAGAACAATGGCTA
ACAAGCACCTCTCATTGTCTCTCTTCCTTGTGCTCCTTGGTCTTTCTGCTTCTCTTGCTTCT
GGTCACCATCACCATCATCACGGATCCGACCCATCCGTGGGAAACAACGTTAAGGAGCTTGT
GGCTTACATCTCCACTTCTGGAGAGAAGGACGCTGGAACCGACGATTACATGTACTTCGGTA
TCAAGACCAAGGATGGAAAGACTCAAGAATGGGAGATGGACAATCCAGGTAACGACTTCATG
GCTGGTAGCAAGGATACTTACACTTTCAAGTTGAAAGACGAGAACCTTAAGATCGACGACAT
CCAGAACATGTGGATTAGGAAACGTAAGTACACCGCCTTCCCAGACGCTTACAAGCCTGAGA
ACATCAAGGTTATCGCTAACGGAAAGGTGGTTGTTGACAAGGATATCAACGAGTGGATTTCT
GGAAACTCCACTTACAACATCAAAGGAGGTTCTGGTGGATCAGGAGGTCCATCTGGAGGTTC
TGGAGGATCCGAGCTTAACGACATCAACAAGATTGAGCTTAAGAACCTCTCCGGAGAGATCA
TCAAGGAGAACGGTAAGGAGGCTATCAAGTACACTTCTTCCGACACCGCTTCCCACAAGGGA
TGGAAGGCCACTCTTTCTGGAACCTTCATCGAAGACCCTCATTCTGACAAGAAGACTGCTTT
GCTTAACCTTGAAGGATTCATCCCATCTGACAAACAGATCTTCGGATCTAAGTACTACGAA
AGATGAAGTGGCCTGAGACTTACAGGATCAACGTGAAGAGCGCTGACGTTAACAACAACATC
AAGATCGCCAACTCTATTCCGAAGAACACTATCGACAAGAAGGACGTGTCCAATTCTATCGG
TTACTCCATCGGAGGTAACATCTCTGTTGAGGGTAAGACTGCTGGTGCTGGAATCAACGCTT
CTTACAACGTTCAGAACACTATCTCCTATGAGCAACCTGACTTCAGAACCATTCAGAGGAAG
GACGATGCTAACCTTGCATCCTGGGACATCAAATTCGTTGAGACTAAGGACGGATACAACAT
CGACTCCTACCATGCTATCTATGGCAACCAGCTCTTCATGAAGAGCAGATTGTACAACAATG
GTGACAAGAACTTCACCGACGATAGGGACCTCTCCACCTTGATCTCTGGTGGATTCTCTCCA
AACATGGCTCTTGCCTTGACCGCTCCTAAGAACGCTAAGGAGTCAGTGATCATCGTTGAATA
CCAGAGGTTCGACAACGACTATATCCTTAACTGGGAGACTACTCAAGCTAGAGGAACTAACA
```

-continued

AGCTTTCTTCAACCTCCGAGTACAACGAGTTTATGTTCAAGATCAACTGGCAGGACCACAAG

ATCGAATACTATCTTTAAGAGCTCGAAGTGACATCACAAAGTTGAAGGTAATAAAGCCAAAT

TAATTAAGACATTTTCATAATGATGTCAAGAATGCAAAGCAAATTGCATAACTGCCTTTATG

CAAAACATTAATATAATATAAATTATAAAGAACTGCGCTCTCTGCTTCTTATTTTCTTAGCT

TCATTTATTAGTCACTAGCTGTTCAGAATTTTCAGTATCTTTTGATATTACTAAGAACCTAA

TCACACAATGTATATTCTTATGCAGGAAAAGCAGAATGCTGAGCTAAAAGAAAGGCTTTTTC

CATTTTCGAGAGACAATGAGAAAGAAGAAGAAGAAGAAGAAGAAGAAGAAGAAAAGAG

TAAATAATAAAGCCCCACAGGAGGCGAAGTTCTTGTAGCTCCATGTTATCTAAGTTATTGAT

ATTGTTTGCCCTATATTTTATTTCTGTCATTGTGTATGTTTTGTTCAGTTTCGATCTCCTTG

CAAAATGCAGAGATTATGAGATGAATAAACTAAGTTATATTATTATACGTGTTAATATTCTC

CTCCTCTCTCTAGCTAGCCTTTTGTTTTCTCTTTTTCTTATTTGATTTTCTTTAAATCAATC

CATTTTAGGAGAGGGCCAGGGAGTGATCCAGCAAAACATGAAGATTAGAAGAAACTTCCCTC

TTTTTTTTCCTGAAAACAATTTAACGTCGAGATTTATCTCTTTTTGTAATGGAATCATTTCT

ACAGTTATGACGAATTCTCGATTAAAAATCCCAATTATATTTGGTCTAATTTAGTTTGGTAT

TGAGTAAAACAAATTCGAACCAAACCAAAATATAAATATATAGTTTTTATATATATGCCTTT

AAGACTTTTTATAGAATTTTCTTTAAAAAATATCTAGAAATATTTGCGACTCTTCTGGCATG

TAATATTTCGTTAAATATGAAGTGCTCCATTTTTATTAACTTTAAATAATTGGTTGTACGAT

CACTTTCTTATCAAGTGTTACTAAAATGCGTCAATCTCTTTGTTCTTCCATATTCATATGTC

AAAATCTATCAAATTCTTATATATCTTTTTCGAATTTGAAGTGAAATTTCGATAATTTAAA

ATTAAATAGAACATATCATTATTTAGGTATCATATTGATTTTTATACTTAATTACTAAATTT

GGTTAACTTTGAAAGTGTACATCAACGAAAAATTAGTCAAACGACTAAAATAAATAAATATC

ATGTGTTATTAAGAAAATTCTCCTATAAGAATATTTTAATAGATCATATGTTTGTAAAAAAA

ATTAATTTTTACTAACACATATATTTACTTATCAAAAATTTGACAAAGTAAGATTAAAATAA

TATTCATCTAACAAAAAAAAAACCAGAAAATGCTGAAAACCCGGCAAAACCGAACCAATCCA

AACCGATATAGTTGGTTTGGTTTGATTTTGATATAAACCGAACCAACTCGGTCCATTTGCAC

CCCTAATCATAATAGCTTTAATATTTCAAGATATTATTAAGTTAACGTTGTCAATATCCTGG

AAATTTTGCAAAATGAATCAAGCCTATATGGCTGTAATATGAATTTAAAAGCAGCTCGATGT

GGTGGTAATATGTAATTTACTTGATTCTAAAAAAATATCCCAAGTATTAATAATTTCTGCTA

GGAAGAAGGTTAGCTACGATTTACAGCAAAGCCAGAATACAAAGAACCATAAAGTGATTGAA

GCTCGAAATATACGAAGGAACAAATATTTTTAAAAAAATACGCAATGACTTGGAACAAAAGA

AAGTGATATATTTTTTGTTCTTAAACAAGCATCCCCTCTAAAGAATGGCAGTTTTCCTTTGC

ATGTAACTATTATGCTCCCTTCGTTACAAAAATTTTGGACTACTATTGGGAACTTCTTCTGA

AAATAGTGGTACCGAGTGTACTTCAAGTCAGTTGGAAATCAATAAAATGATTATTTTATGAA

TATATTTCATTGTGCAAGTAGATAGAAATTAGATATGTTAGATAACACACGAATAAACAAA

AAAACACAATCCAAAACAAACACCCCAAACAAAATAACACTATATATATCCTCGTATGAGGA

GAGGCACGTTCAGTGACTCGACGATTCCCGAGCAAAAAAGTCTCCCCGTCACACATATAGT

GGGTGACGCAATTATCTTCAAAGTAATCCTTCTGTTGACTTGTCATTGATAACATCCAGTCT

TCGTCAGGATTGCAAAGAATTATAGAAGGGATCCCACCTTTTATTTTCTTCTTTTTTCCATA

TTTAGGGTTGACAGTGAAATCAGACTGGCAACCTATTAATTGCTTCCACAATGGGACGAACT

TGAAGGGGATGTCGTCGATGATATTATAGGTGGCGTGTTCATCGTAGTTGGTGAAGTCGATG

GTCCCGTTCCAGTAGTTGTGTCGCCCGAGACTTCTAGCCCAGGTGGTCTTTCCGGTACGAGT

-continued

```
TGGTCCGCAGATGTAGAGGCTGGGGTGTCTGACCCCAGTCCTTCCCTCATCCTGGTTAGATC
GGCCATCCACTCAAGGTCAGATTGTGCTTGATCGTAGGAGACAGGATGTATGAAAGTGTAGG
CATCGATGCTTACATGATATAGGTGCGTCTCTCTCCAGTTGTGCAGATCTTCGTGGCAGCGG
AGATCTGATTCTGTGAAGGGCGACACGTACTGCTCAGGTTGTGGAGGAAATAATTTGTTGGC
TGAATATTCCAGCCATTGAAGCTTTGTTGCCCATTCATGAGGGAACTCTTCTTTGATCATGT
CAAGATACTCCTCCTTAGACGTTGCAGTCTGGATAATAGTTCGCCATCGTGCGTCAGATTTG
CGAGGAGACACCTTATGATCTCGGAAATCTCCTCTGGTTTTAATATCTCCGTCCTTTGATAT
GTAATCAAGGACTTGTTTAGAGTTTCTAGCTGGCTGGATATTAGGGTGATTTCCTTCAAAAT
CGAAAAAAGAAGGATCCCTAATACAAGGTTTTTTATCAAGCTGGATAAGAGCATGATAGTGG
GTAGTGCCATCTTGATGAAGCTCAGAAGCAACACCAAGGAAGAAAATAAGAAAAGGTGTGAG
TTTCTCCCAGAGAAACTGGAATAAATCATCTCTTTGAGATGAGCACTTGGGGTAGGTAAGGA
AAACATATTTAGATTGGAGTCTGAAGTTCTTGCTAGCAGAAGGCATGTTGTTGTGACTCCGA
GGGGTTGCCTCAAACTCTATCTTATAACCGGCGTGGAGGCATGGAGGCAAGGGCATTTTGGT
AATTTAAGTAGTTAGTGGAAAATGACGTCATTTACTTAAAGACGAAGTCTTGCGACAAGGGG
GGCCCACGCCGAATTTTAATATTACCGGCGTGGCCCCACCTTATCGCGAGTGCTTTAGCACG
AGCGGTCCAGATTTAAAGTAGAAAAGTTCCCGCCCACTAGGGTTAAAGGTGTTCACACTATA
AAAGCATATACGATGTGATGGTATTTGATGGAGCGTATATTGTATCAGGTATTTCCGTCGGA
TACGAATTATTCGTACGGCCGGACCGGTCCCCTAGGCCGGCCAATTCGAGATCGGCCGCGGC
TGAGTGGCTCCTTCAATCGTTGCGGTTCTGTCAGTTCCAAACGTAAAACGGCTTGTCCCGCG
TCATCGGCGGGGGTCATAACGTGACTCCCTTAATTCTCCGCTCATGATCAGATTGTCGTTTC
CCGCCTTCAGTTTAAACTATCAGTGTTTGACAGGATATATTGGCGGGTAAACCTAAGAGAAA
AGAGCGTTTATTAGAATAATCGGATATTTAAAAGGGCGTGAAAAGGTTTATCCGTTCGTCCA
TTTGTATGTGCATGCCAACCACAGGGTTCCCCAGATCTGGCGCCGGCCAGCGAGACGAGCAA
GATTGGCCGCCGCCCGAAACGATCCGACAGCGCGCCCAGCACAGGTGCGCAGGCAAATTGCA
CCAACGCATACAGCGCCAGCAGAATGCCATAGTGGGCGGTGACGTCGTTCGAGTGAACCAGA
TCGCGCAGGAGGCCCGGCAGCACCGGCATAATCAGGCCGATGCCGACAGCGTCGAGCGCGAC
AGTGCTCAGAATTACGATCAGGGGTATGTTGGGTTTCACGTCTGGCCTCCGGAGACTGTCAT
ACGCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGT
TTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAG
TTCGGTGTAGGTCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACAGAGTT
CTTGAAGTGGTGGCCTAACTACGGCTACACTAGAAGGACAGTATTTGGTATCTGCGCTCTGC
TGAAGCCAGTTACCTTCGGAAAAGAGTTGGTAGCTCTTGATCCGGCAAACAAACCACCGCT
GGTAGCGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTAAGGGA
TTTTGGTCATGAGATTATCAAAAAGGATCTTCACCTAGATCCTTTTAAATTAAAAATGAAGT
TTTAAATCAATCTAAAGTATATATGAGTAAACTTGGTCTGCAGTTGCCATGTTTTACGGCAG
```

-continued

```
TGAGAGCAGAGATAGCGCTGATGTCCGGCGGTGCTTTTGCCGTTACGCACCACCCCGTCAGT
AGCTGAACAGGAGGGACAGCTGATAGACACAGAAGCCACTGGAGCACCTCAAAAACACCATC
ATACACTAAATCAGTAAGTTGGCAGCATCACCCATAATTGTGGTTTCAAAATCGGCTCCGTC
GATACTATGTTATACGCCAACTTTGAAAACAACTTTGAAAAAGCTGTTTTCTGGTATTTAAG
GTTTTAGAATGCAAGGAACAGTGAATTGGAGTTCGTCTTGTTATAATTAGCTTCTTGGGGTA
TCTTTAAATACTGTAGAAAAGAGGAAGGAAATAATAAATGGCTAAAATGAGAATATCACCGG
AATTGAAAAAACTGATCGAAAAATACCGCTGCGTAAAAGATACGGAAGGAATGTCTCCTGCT
AAGGTATATAAGCTGGTGGGAGAAAATGAAAACCTATATTTAAAAATGACGGACAGCCGGTA
TAAAGGGACCACCTATGATGTGGAACGGGAAAAGGACATGATGCTATGGCTGGAAGGAAAGC
TGCCTGTTCCAAAGGTCCTGCACTTTGAACGGCATGATGGCTGGAGCAATCTGCTCATGAGT
GAGGCCGATGGCGTCCTTTGCTCGGAAGAGTATGAAGATGAACAAAGCCCTGAAAAGATTAT
CGAGCTGTATGCGGAGTGCATCAGGCTCTTTCACTCCATCGACATATCGGATTGTCCCTATA
CGAATAGCTTAGACAGCCGCTTAGCCGAATTGGATTACTTACTGAATAACGATCTGGCCGAT
GTGGATTGCGAAAACTGGGAAGAAGACACTCCATTTAAAGATCCGCGCGAGCTGTATGATTT
TTTAAAGACGGAAAAGCCCGAAGAGGAACTTGTCTTTTCCCACGGCGACCTGGGAGACAGCA
ACATCTTTGTGAAAGATGGCAAAGTAAGTGGCTTTATTGATCTTGGGAGAAGCGGCAGGGCG
GACAAGTGGTATGACATTGCCTTCTGCGTCCGGTCGATCAGGGAGGATATCGGGAAGAACA
GTATGTCGAGCTATTTTTTGACTTACTGGGGATCAAGCCTGATTGGGAGAAAATAAAATATT
ATATTTTACTGGATGAATTGTTTTAGTACCTAGATGTGGCGCAACGATGCCGGCGACAAGCA
GGAGCGCACCGACTTCTTCCGCATCAAGTGTTTTGGCTCTCAGGCCGAGGCCCACGGCAAGT
ATTTGGGCAAGGGGTCGCTGGTATTCGTGCAGGGCAAGATTCGGAATACCAAGTACGAGAAG
GACGGCCAGACGGTCTACGGGACCGACTTCATTGCCGATAAGGTGGATTATCTGGACACCAA
GGCACCAGGCGGGTCAAATCAGGAATAAGGGCACATTGCCCCGGCGTGAGTCGGGGCAATCC
CGCAAGGAGGGTGAATGAATCGGACGTTTGACCGGAAGGCATACAGGCAAGAACTGATCGAC
GCGGGGTTTTCCGCCGAGGATGCCGAAACCATCGCAAGCCGCACCGTCATGCGTGCGCCCCG
CGAAACCTTCCAGTCCGTCGGCTCGATGGTCCAGCAAGCTACGGCCAAGATCGAGCGCGACA
GCGTGCAACTGGCTCCCCCTGCCCTGCCCGCGCCATCGGCCGCCGTGGAGCGTTCGCGTCGT
CTCGAACAGGAGGCGGCAGGTTTGGCGAAGTCGATGACCATCGACACGCGAGGAACTATGAC
GACCAAGAAGCGAAAAACCGCCGGCGAGGACCTGGCAAAACAGGTCAGCGAGGCCAAGCAGG
CCGCGTTGCTGAAACACACGAAGCAGCAGATCAAGGAAATGCAGCTTTCCTTGTTCGATATT
GCGCCGTGGCCGGACACGATGCGAGCGATGCCAAACGACACGGCCCGCTCTGCCCTGTTCAC
CACGCGCAACAAGAAAATCCCGCGCGAGGCGCTGCAAAACAAGGTCATTTTCCACGTCAACA
AGGACGTGAAGATCACCTACACCGGCGTCGAGCTGCGGGCCGACGATGACGAACTGGTGTGG
CAGCAGGTGTTGGAGTACGCGAAGCGCACCCCTATCGGCGAGCCGATCACCTTCACGTTCTA
CGAGCTTTGCCAGGACCTGGGCTGGTCGATCAATGGCCGGTATTACACGAAGGCCGAGGAAT
GCCTGTCGCGCCTACAGGCGACGGCGATGGGCTTCACGTCCGACCGCGTTGGGCACCTGGAA
TCGGTGTCGCTGCTGCACCGCTTCCGCGTCCTGGACCGTGGCAAGAAAACGTCCCGTTGCCA
GGTCCTGATCGACGAGGAAATCGTCGTGCTGTTTGCTGGCGACCACTACACGAAATTCATAT
GGGAGAAGTACCGCAAGCTGTCGCCGACGGCCCGACGGATGTTCGACTATTTCAGCTCGCAC
CGGGAGCCGTACCCGCTCAAGCTGGAAACCTTCCGCCTCATGTGCGGATCGGATTCCACCCG
CGTGAAGAAGTGGCGCGAGCAGGTCGGCGAAGCCTGCGAAGAGTTGCGAGGCAGCGGCCTGG
```

-continued

```
TGGAACACGCCTGGGTCAATGATGACCTGGTGCATTGCAAACGCTAGGGCCTTGTGGGGTCA
GTTCCGGCTGGGGGTTCAGCAGCCAGCGCTTTACTGGCATTTCAGGAACAAGCGGGCACTGC
TCGACGCACTTGCTTCGCTCAGTATCGCTCGGGACGCACGGCGCGCTCTACGAACTGCCGAT
AAACAGAGGATTAAAATTGACAATTCAATGGCAAGGACTGCCAGCGCTGCCATTTTTGGGGT
GAGGCCGTTCGCGGCCGAGGGGCGCAGCCCCTGGGGGGATGGGAGGCCCGCGTTAGCGGGCC
GGGAGGGTTCGAGAAGGGGGGGCACCCCCCTTCGGCGTGCGCGGTCACGCGCACAGGGCGCA
GCCCTGGTTAAAAACAAGGTTTATAAATATTGGTTTAAAAGCAGGTTAAAAGACAGGTTAGC
GGTGGCCGAAAAACGGGCGGAAACCCTTGCAAATGCTGGATTTTCTGCCTGTGGACAGCCCC
TCAAATGTCAATAGGTGCGCCCCTCATCTGTCAGCACTCTGCCCCTCAAGTGTCAAGGATCG
CGCCCCTCATCTGTCAGTAGTCGCGCCCCTCAAGTGTCAATACCGCAGGGCACTTATCCCCA
GGCTTGTCCACATCATCTGTGGGAAACTCGCGTAAAATCAGGCGTTTTCGCCGATTTGCGAG
GCTGGCCAGCTCCACGTCGCCGGCCGAAATCGAGCCTGCCCCTCATCTGTCAACGCCGCGCC
GGGTGAGTCGGCCCCTCAAGTGTCAACGTCCGCCCCTCATCTGTCAGTGAGGGCCAAGTTTT
CCGCGAGGTATCCACAACGCCGGCGGCCGCGGTGTCTCGCACACGGCTTCGACGGCGTTTCT
GGCGCGTTTGCAGGGCCATAGACGGCCGCCAGCCCAGCGGCGAGGGCAACCAGCCCGGTGAG
CGTCGCAAAGGCGCTCGGTCTTGCCTTGCTCGTCGAGATCTGGGGTCGATCAGCCGGGGATG
CATCAGGCCGACAGTCGGAACTTCGGGTCCCCGACCTGTACCATTCGGTGAGCAATGGATAG
GGGAGTTGATATCGTCAACGTTCACTTCTAAAGAAATAGCGCCACTCAGCTTCCTCAGCGGC
TTTATCCAGCGATTTCCTATTATGTCGGCATAGTTCTCAAGATCGACAGCCTGTCACGGTTA
AGCGAGAAATGAATAAGAAGGCTGATAATTCGGATCTCTGCGAGGGAGATGATATTTGATGA
CAGGCAGCAACGCTCTGTCATCGTTACAATCAACATGCTACCCTCCGCGAGATCATCCGTGT
TTCAAACCCGGCAGCTTAGTTGCCGTTCTTCCGAATAGCATCGGTAACATGAGCAAAGTCTG
CCGCCTTACAACGGCTCTCCCGCTGACGCCGTCCCGGACTGATGGGCTGCCTGTATCGAGTG
GTGATTTTGTGCCGAGCTGCCGGTCGGGGAGCTGTTGGCTGGCTGGTGGCAGGATATATTGT
GGTGTAAACAAATTGAGGCTTAGACAACTTAATAACACATTGCGGAGGTTTTTAATGTACTG
GGGTGGTTTTTCTTTTCACCAGTGAGACGGGCAACAGCTGATTGCCCTTCACCGCCTGGCCC
TGAGAGAGTTGCAGCAAGCGGTCCACGCTGGTTTGCCCCAGCAGGCGAAAATCCTGTTTGAT
GGTGGTTCCGAAATCGGCAAAATCCCTTATAAATCAAAAGAATAGCCCGAGATAGGGTTGAG
TGTTGTTCCAGTTTGGAACAAGAGTCCACTATTAAAGAACGTGGACTCCAACGTCAAAGGGC
GAAAAACCGTCTATCAGGGCGATGGCCCACTACGTGAACCATCACCCAAATCAAGTTTTTTG
GGGTCGAGGTGCCGTAAAGCACTAAATCGGAACCCTAAAGGGAGCCCCCGATTTAGAGCTTG
ACGGGGAAAGCCGGCGAACGTGGCGAGAAAGGAAGGGAAGAAAGCGAAAGGAGCGGGCGCCA
TTCAGGCTGCGCAACTGTTGGGAAGGG
```

The sequence indicated in bold above is the portion that encodes the fusion protein:

(SEQ ID NO: 6)
```
ATGGCTAACAAGCACCTCTCATTGTCTCTCTTCCTTGTGCTCCTTGGTCTTTCTGCT
TCTCTTGCTTCTGGTCACCATCACCATCATCACGGATCCGACCCATCCGTGGGAAACAACGT
TAAGGAGCTTGTGGCTTACATCTCCACTTCTGGAGAGAAGGACGCTGGAACCGACGATTACA
TGTACTTCGGTATCAAGACCAAGGATGGAAAGACTCAAGAATGGGAGATGGACAATCCAGGT
```

```
-continued
AACGACTTCATGGCTGGTAGCAAGGATACTTACACTTTCAAGTTGAAAGACGAGAACCTTAA

GATCGACGACATCCAGAACATGTGGATTAGGAAACGTAAGTAGACCGCCTTCCCAGACGCTT

ACAAGCCTGAGAACATCAAGGTTATCGCTAACGGAAAGGTGGTTGTTGACAAGGATATCAAC

GAGTGGATTTCTGGAAACTCCACTTACAACATCAAAGGAGGTTCTGGTGGATCAGGAGGTCC

ATCTGGAGGTTCTGGAGGATCCGAGCTTAACGACATCAACAAGATTGAGCTTAAGAACCTCT

CCGGAGAGATCATCAAGGAGAACGGTAAGGAGGCTATCAAGTACACTTCTTCCGACACCGCT

TCCCACAAGGGATGGAAGGCCACTCTTTCTGGAACCTTCATCGAAGACCCTCATTCTGACAA

GAAGACTGCTTTGCTTAACCTTGAAGGATTCATCCCATCTGACAAACAGATCTTCGGATCTA

AGTACTACGGAAAGATGAAGTGGCCTGAGACTTACAGGATCAACGTGAAGAGCGCTGACGTT

AACAACAACATCAAGATCGCCAACTCTATTCCGAAGAACACTATCGACAAGAAGGACGTGTC

CAATTCTATCGGTTACTCCATCGGAGGTAACATCTCTGTTGAGGGTAAGACTGCTGGTGCTG

GAATCAACGCTTCTTACAACGTTCAGAACACTATCTCCTATGAGCAACCTGACTTCAGAACC

ATTCAGAGGAAGGACGATGCTAACCTTGCATCCTGGGACATCAAATTCGTTGAGACTAAGGA

CGGATACAACATCGACTCCTACCATGCTATCTATGGCAACCAGCTCTTCATGAAGAGCAGAT

TGTACAACAATGGTGACAAGAACTTCACCGACGATAGGGACCTCTCCACCTTGATCTCTGGT

GGATTCTCTCCAAACATGGCTCTTGCCTTGACCGCTCCTAAGAACGCTAAGGAGTCAGTGAT

CATCGTTGAATACCAGAGGTTCGACAACGACTATATCCTTAACTGGGAGACTACTCAAGCTA

GAGGAACTAACAAGCTTTCTTCAACCTCCGAGTAGAACGAGTTTATGTTCAAGATCAACTGG

CAGGACCACAAGATCGAATACTATCTTTAA
```

The proteins of the present invention may be expressed from an isolated DNA sequence encoding the protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell or bacteriophage. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, functional RNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

The term "chimeric" refers to any gene or DNA that contains 1) DNA sequences, including regulatory and coding sequences that are not found together in nature or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, DNA that is either heterologous or homologous to the DNA of a particular cell to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences as described, for example, in Sambrook and Russell, *Molecular Cloning: A Laboratory Manual*, Cold Spring Harbor, NY: Cold Spring Harbor Laboratory Press ($3^{rd}$ edition, 2001).

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

Expression Cassettes

In certain embodiments, the present invention provides an expression cassette comprising the nucleic acid described herein and a promoter.

In certain embodiments, the promoter is a plant promoter.

In certain embodiments, the plant promoter is operable in corn or rice.

In certain embodiments, the plant promoter is operable in seed tissue.

In certain embodiments, the seed tissue is embryo or endosperm tissue.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a known mathematical algorithm. Computer implementations of these mathematical algorithms can be utilized for comparison of sequences to determine sequence identity. Such implementations include, but are not limited to: CLUSTAL in the PC/Gene program (available from Intelligenetics, Mountain View, California); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wisconsin, USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world-wide-web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about SEC lower than the $T_m$ for the specific sequence at a defined ionic strength and pH.

An example of highly stringent wash conditions is 0.15 M NaCl at 72EC for about 15 minutes. An example of stringent wash conditions is a 0.2×SSC wash at 65EC for 15 minutes. Often, a high stringency wash is preceded by a low stringency wash to remove background probe signal. An example medium stringency wash for a duplex of, e.g., more than 100 nucleotides, is 1×SSC at 45EC for 15 minutes. An example low stringency wash for a duplex of, e.g., more than 100 nucleotides, is 4-6×SSC at 40EC for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30EC and at least about 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

In certain embodiments, the nucleic acid sequences are the following:

Fusion protein cds, with signal peptide:

(SEQ ID NO: 7)

ATGGCTAACAAGCACCTCTCATTGTCTCTCTTCCTTGTGCTCCTTGGTCTTTCTGCTTCTCT

TGCTTCTGGTCACCATCACCATCATCACGGATCCGACCCATCCGTGGGAAACAACGTTAAGG

AGCTTGTGGCTTACATCTCCACTTCTGGAGAGAAGGACGCTGGAACCGACGATTACATGTAC

TTCGGTATCAAGACCAAGGATGGAAAGACTCAAGAATGGGAGATGGACAATCCAGGTAACGA

CTTCATGGCTGGTAGCAAGGATACTTACACTTTCAAGTTGAAAGACGAGAACCTTAAGATCG

ACGAGATCCAGAACATGTGGATTAGGAAACGTAAGTAGACCGCCTTCCCAGACGCTTACAAG

CCTGAGAACATCAAGGTTATCGCTAACGGAAAGGTGGTTGTTGACAAGGATATCAACGAGTG

GATTTCTGGAAACTCCACTTACAACATCAAAGGAGGTTCTGGTGGATCAGGAGGTCCATCTG

GAGGTTCTGGAGGATCCGAGCTTAACGACATCAACAAGATTGAGCTTAAGAACCTCTCCGGA

GAGATCATCAAGGAGAACGGTAAGGAGGCTATCAAGTACACTTCTTCCGACACCGCTTCCCA

CAAGGGATGGAAGGCCACTCTTTCTGGAACCTTCATCGAAGACCCTCATTCTGACAAGAAGA

-continued

CTGCTTTGCTTAACCTTGAAGGATTCATCCCATCTGACAAACAGATCTTCGGATCTAAGTAC

TACGGAAAGATGAAGTGGCCTGAGACTTACAGGATCAACGTGAAGAGCGCTGACGTTAACAA

CAACATCAAGATCGCCAACTCTATTCCGAAGAACACTATCGACAAGAAGGACGTGTCCAATT

CTATCGGTTACTCCATCGGAGGTAACATCTCTGTTGAGGGTAAGACTGCTGGTGCTGGAATC

AACGCTTCTTACAACGTTCAGAACACTATCTCCTATGAGCAACCTGACTTCAGAACCATTCA

GAGGAAGGACGATGCTAACCTTGCATCCTGGGACATCAAATTCGTTGAGACTAAGGACGGAT

ACAACATCGACTCCTACCATGCTATCTATGGCAACCAGCTCTTCATGAAGAGCAGATTGTAC

AACAATGGTGACAAGAACTTCACCGACGATAGGGACCTCTCCACCTTGATCTCTGGTGGATT

CTCTCCAAACATGGCTCTTGCCTTGACCGCTCCTAAGAACGCTAAGGAGTCAGTGATCATCG

TTGAATACCAGAGGTTCGACAACGACTATATCCTTAACTGGGAGACTACTCAAGCTAGAGGA

ACTAACAAGCTTTCTTCAACCTCCGAGTACAACGAGTTTATGTTCAAGATCAACTGGCAGGA

CCACAAGATCGAATACTATCTT

Fusion protein cds, without signal peptide:
(SEQ ID NO: 8)
ATGGCTCACCATCACCATCATCACGGATCCGACCCATCCGTGGGAAACAACGTTAAGGAGCT

TGTGGCTTACATCTCCACTTCTGGAGAGAAGGACGCTGGAACCGACGATTACATGTACTTCG

GTATCAAGACCAAGGATGGAAAGACTCAAGAATGGGAGATGGACAATCCAGGTAACGACTTC

ATGGCTGGTAGCAAGGATACTTACACTTTCAAGTTGAAAGACGAGAACCTTAAGATCGACGA

CATCCAGAACATGTGGATTAGGAAACGTAAGTACACCGCCTTCCCAGACGCTTACAAGCCTG

AGAACATCAAGGTTATCGCTAACGGAAAGGTGGTTGTTGACAAGGATATCAACGAGTGGATT

TCTGGAAACTCCACTTACAACATCAAAGGAGGTTCTGGTGGATCAGGAGGTCCATCTGGAGG

TTCTGGAGGATCCGAGCTTAACGACATCAACAAGATTGAGCTTAAGAACCTCTCCGGAGAGA

TCATCAAGGAGAACGGTAAGGAGGCTATCAAGTACACTTCTTCCGACACCGCTTCCCACAAG

GGATGGAAGGCCACTCTTTCTGGAACCTTCATCGAAGACCCTCATTCTGACAAGAAGACTGC

TTTGCTTAACCTTGAAGGATTCATCCCATCTGACAAACAGATCTTCGGATCTAAGTACTACG

GAAAGATGAAGTGGCCTGAGACTTACAGGATCAACGTGAAGAGCGCTGACGTTAACAACAAC

ATCAAGATCGCCAACTCTATTCCGAAGAACACTATCGACAAGAAGGACGTGTCCAATTCTAT

CGGTTACTCCATCGGAGGTAACATCTCTGTTGAGGGTAAGACTGCTGGTGCTGGAATCAACG

CTTCTTACAACGTTCAGAACACTATCTCCTATGAGCAACCTGACTTCAGAACCATTCAGAGG

AAGGACGATGCTAACCTTGCATCCTGGGACATCAAATTCGTTGAGACTAAGGACGGATACAA

CATCGACTCCTACCATGCTATCTATGGCAACCAGCTCTTCATGAAGAGCAGATTGTACAACA

ATGGTGACAAGAACTTCACCGACGATAGGGACCTCTCCACCTTGATCTCTGGTGGATTCTCT

CCAAACATGGCTCTTGCCTTGACCGCTCCTAAGAACGCTAAGGAGTCAGTGATCATCGTTGA

ATACCAGAGGTTCGACAACGACTATATCCTTAACTGGGAGACTACTCAAGCTAGAGGAACTA

ACAAGCTTTCTTCAACCTCCGAGTACAACGAGTTTATGTTCAAGATCAACTGGCAGGACCAC

AAGATCGAATACTATCTT

6His-plcC, with signal peptide:
(SEQ ID NO: 9)
ATGGCTAACAAGCACCTCTCATTGTCTCTCTTCCTTGTGCTCCTTGGTCTTTCTGCTTCTCT

TGCTTCTGGTCACCATCACCATCATCACGGATCCGACCCATCCGTGGGAAACAACGTTAAGG

AGCTTGTGGCTTACATCTCCACTTCTGGAGAGAAGGACGCTGGAACCGACGATTACATGTAC

TTCGGTATCAAGACCAAGGATGGAAAGACTCAAGAATGGGAGATGGACAATCCAGGTAACGA

-continued

CTTCATGGCTGGTAGCAAGGATACTTACACTTTCAAGTTGAAAGACGAGAACCTTAAGATCG

ACGACATCCAGAACATGTGGATTAGGAAACGTAAGTAGACCGCCTTCCCAGACGCTTAGAAG

CCTGAGAACATCAAGGTTATCGCTAACGGAAAGGTGGTTGTTGACAAGGATATCAACGAGTG

GATTTCTGGAAACTCCACTTACAACATCAAA

6His-plcC, without signal peptide:
(SEQ ID NO: 10)
ATGGCTCACCATCACCATCATCACGGATCCGACCCATCCGTGGGAAACAACGTTAAGGAGCT

TGTGGCTTACATCTCCACTTCTGGAGAGAAGGACGCTGGAACCGACGATTACATGTACTTCG

GTATCAAGACCAAGGATGGAAAGACTCAAGAATGGGAGATGGACAATCCAGGTAACGACTTC

ATGGCTGGTAGCAAGGATACTTACACTTTCAAGTTGAAAGACGAGAACCTTAAGATCGACGA

CATCCAGAACATGTGGATTAGGAAACGTAAGTACACCGCCTTCCCAGACGCTTACAAGCCTG

AGAACATCAAGGTTATCGCTAACGGAAAGGTGGTTGTTGACAAGGATATCAACGAGTGGATT

TCTGGAAACTCCACTTACAACATCAAA

6His-netB, with signal peptide:
(SEQ ID NO: 11)
ATGGCTAACAAGCACCTCTCATTGTCTCTCTTCCTTGTGCTCCTTGGTCTTTCTGCTTCTCT

TGCTTCTGGTCACCATCACCATCATCACGGATCCGAGCTTAACGACATCAACAAGATTGAGC

TTAAGAACCTCTCCGGAGAGATCATCAAGGAGAACGGTAAGGAGGCTATCAAGTACACTTCT

TCCGACACCGCTTCCCACAAGGGATGGAAGGCCACTCTTTCTGGAACCTTCATCGAAGACCC

TCATTCTGACAAGAAGACTGCTTTGCTTAACCTTGAAGGATTCATCCCATCTGACAAACAGA

TCTTCGGATCTAAGTACTACGGAAAGATGAAGTGGCCTGAGACTTACAGGATCAACGTGAAG

AGCGCTGACGTTAACAACAACATCAAGATCGCCAACTCTATTCCGAAGAACACTATCGACAA

GAAGGACGTGTCCAATTCTATCGGTTACTCCATCGGAGGTAACATCTCTGTTGAGGGTAAGA

CTGCTGGTGCTGGAATCAACGCTTCTTACAACGTTCAGAACACTATCTCCTATGAGCAACCT

GACTTCAGAACCATTCAGAGGAAGGACGATGCTAACCTTGCATCCTGGGACATCAAATTCGT

TGAGACTAAGGACGGATACAACATCGACTCCTACCATGCTATCTATGGCAACCAGCTCTTCA

TGAAGAGCAGATTGTACAACAATGGTGACAAGAACTTCACCGACGATAGGGACCTCTCCACC

TTGATCTCTGGTGGATTCTCTCCAAACATGGCTCTTGCCTTGACCGCTCCTAAGAACGCTAA

GGAGTCAGTGATCATCGTTGAATACCAGAGGTTCGACAACGACTATATCCTTAACTGGGAGA

CTACTCAAGCTAGAGGAACTAACAAGCTTTCTTCAACCTCCGAGTAGAACGAGTTTATGTTC

AAGATCAACTGGCAGGACCACAAGATCGAATACTATCTT

6His-netB, without signal peptide:
(SEQ ID NO: 12)
ATGGCTCACCATCACCATCATCACGGATCCGAGCTTAACGACATCAACAAGATTGAGCTTAA

GAACCTCTCCGGAGAGATCATCAAGGAGAACGGTAAGGAGGCTATCAAGTACACTTCTTCCG

ACACCGCTTCCCACAAGGGATGGAAGGCCACTCTTTCTGGAACCTTCATCGAAGACCCTCAT

TCTGACAAGAAGACTGCTTTGCTTAACCTTGAAGGATTCATCCCATCTGACAAACAGATCTT

CGGATCTAAGTACTACGGAAAGATGAAGTGGCCTGAGACTTACAGGATCAACGTGAAGAGCG

CTGACGTTAACAACAACATCAAGATCGCCAACTCTATTCCGAAGAACACTATCGACAAGAAG

GACGTGTCCAATTCTATCGGTTACTCCATCGGAGGTAACATCTCTGTTGAGGGTAAGACTGC

TGGTGCTGGAATCAACGCTTCTTACAACGTTCAGAACACTATCTCCTATGAGCAACCTGACT

TCAGAACCATTCAGAGGAAGGACGATGCTAACCTTGCATCCTGGGACATCAAATTCGTTGAG

ACTAAGGACGGATACAACATCGACTCCTACCATGCTATCTATGGCAACCAGCTCTTCATGAA

GAGCAGATTGTAGAACAATGGTGACAAGAACTTCACCGACGATAGGGACCTCTCCACCTTGA

-continued

```
TCTCTGGTGGATTCTCTCCAAACATGGCTCTTGCCTTGACCGCTCCTAAGAACGCTAAGGAG

TCAGTGATCATCGTTGAATACCAGAGGTTCGACAACGACTATATCCTTAACTGGGAGACTAG

TCAAGCTAGAGGAACTAACAAGCTTTCTTCAACCTCCGAGTAGAACGAGTTTATGTTCAAGA

TCAACTGGCAGGACCACAAGATCGAATACTATCTT
```

Vectors

In certain embodiments, the present invention provides a recombinant vector comprising the expression cassette described herein and a vector.

In certain embodiments, the vector is a viral vector.

In certain embodiments, the vector is a bean yellow dwarf virus replicon.

In certain embodiments, the vector is pBYR2eK2M-6HplcCnetB. (SEQ ID NO: 14 and FIG. 6).

A "vector" is defined to include, inter alia, any plasmid, cosmid, phage or binary vector in double or single stranded linear or circular form which may or may not be self transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

Plant Cells and Animal Feed

In certain embodiments, the present invention provides a plant cell comprising the antigenic protein described herein, the nucleic acid described herein, the expression cassette described herein or the recombinant vector described herein.

In certain embodiments, the plant is a corn or rice cell.

In certain embodiments, the plant cell further comprises an E. coli heat-labile enterotoxin (LT) and/or a cholera toxin (CT).

In certain embodiments, the present invention provides animal feed comprising the plant cell described herein.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

Vaccines

In certain embodiments, the present invention provides a vaccine comprising the antigenic protein described herein, the nucleic acid described herein, the expression cassette described herein, the recombinant vector described herein, the plant cell described herein, or the animal feed described herein.

The fusion antigen was readily purified using metal affinity chromatography, and used for chicken immunization experiments. The data indicate that the plant-made fusion protein was immunogenic and protective. Evidence was observed on western blots that the PlcC-NetB accumulated in several glycosylated forms. A search of the PlcC-NetB amino acid sequence for consensus Asn-linked glycosylation sites (Asn-X-Ser/Thr) showed one site in the PlcC and four sites in the NetB domain. Mapping of these sites on the 3-dimensional structures of Plc and NetB showed that they mostly occur in surface loops, and thus probably would not interfere with correct folding of the proteins or impair the antigen structure of protective epitopes. In some cases, such eukaryotic glycosylation was shown to be either neutral in effect or enhance immunogenicity of plant-made antigens. However, it is difficult to predict the effects of glycosylation on the immunogenicity of PlcC-NetB. The preliminary study showed it is immunogenic in chickens, it is possible that a non-glycosylated protein will be even more potent.

Thus, a new expression vector was constructed that lacks the N-terminal signal sequence, which resulted in cytosolic accumulation and thus unglycosylated antigen. The glycosylated and unglycosylated antigens are used in further studies to test immunogenicity and protection in chickens. Several mutant forms of NetB have been studied and showed reduced toxicity and may retain protective immunogenicity. Single amino acid substitutions in the rim loop region that significantly reduce its toxicity include Y191A, R200A, W257A, W262A S254L, R230Q and W287R. Some of these were shown to retain the ability to generate protective immune responses, including W262A and S254L. Thus it is reasonable to contemplate the use of multiple different mutations in the NetB component of the PlcCNetB fusion protein, in order to maximize its safety. For production of the fusion protein in seeds of corn or rice, stable transgenic lines must be developed. The expression construct would use an appropriate promoter that will drive strong expression in a seed tissue, such as embryo or endosperm tissues. Agrobacterium-mediated delivery of DNA to embryogenic cell cultures enables creation of stably transformed whole plants that transmit the transgenes to sexual progeny.

One may consider the co-delivery of a mucosal adjuvant to enhance immunogenicity of the PlcC-NetB antigens. The E. coli heat-labile enterotoxin (LT) and related cholera toxin (CT) are potent stimulators of mucosal immunity. LT and mutants thereof (including LTA S63K and A72R have been expressed in transgenic tobacco cells, and were well tolerated and immunogenic in chickens by oral or parenteral delivery. Orally immunogenic LT-B was expressed in transgenic corn; and CT-B was expressed in transgenic rice.

Methods for milling and formulating corn and rice for oral delivery are well developed and convenient.

Methods of Administration

In certain embodiments, the present invention provides a method of protecting an avian species from *C. perfringens* infections comprising administering the vaccine described herein.

In certain embodiments, the avian species is chicken, turkey, duck or ostrich.

In certain embodiments, the avian is a chicken or turkey.

The present invention also provides a method of protecting poultry by administering to the poultry an immunologically protective amount of a vaccine of the present invention. As used herein, the term "immunologically protective" means that the vaccine is effective in inducing a protective immune response. An immunological response to a composition or vaccine is the development in the host of a cellular and/or antibody-mediated immune response to the protein or vaccine of interest. Usually, such a response consists of the subject producing antibodies, B cell, helper T cells, suppressor T cells, and/or cytotoxic T cells directed specifically to an antigen or antigens included in the composition or vaccine of interest.

The fusion can be purified and used to inject birds. Injections can be given to hens prior to lay, to enhance immunity of chicks during the first 2-3 weeks of life by passive transfer of antibodies against the fusion protein. In certain embodiments, a suitable adjuvant is used. For example, saponin adjuvant such as Quil A, various oil emulsion adjuvants such as water in oil or water in oil in water formulations are used.

The agents of the invention are preferably administered so as to result in a reduction in at least one symptom associated with a disease. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems, which are well known to the art.

Administration of therapeutic agents may be accomplished through the administration of the therapeutic agent, such as a fusion protein. Pharmaceutical formulations, dosages and routes of administration for peptide are generally known.

The present invention envisions treating uveitis in a mammal by the administration of an agent, e.g., a fusion protein. Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules, as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intraocular routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions such as phosphate buffered saline solutions pH 7.0-8.0 saline solutions and water.

As used herein, the term "therapeutic agent" refers to a fusion protein agent or material containing the fusion protein that has a beneficial effect on the mammalian recipient. "Treating" as used herein refers to preventing infection of *C. perfringens* infection.

The present invention also provides a method of protecting poultry by administering a vaccine that is effective in inducing cellular and humoral immunity and that contains a biological agent or microbial component that is effective in stimulating a protective cellular and humoral immune response to *C. perfringens*.

The purified protein can also be used for in ovo vaccination. Again, a suitable adjuvant may be used to enhance immunogenicity, as discussed above. The vaccine of the present invention can be administered via conventional modes of administration or in ovo. Methods of in ovo immunization are set forth, for example, in U.S. Pat. No.

6,048,535. Vaccination can be performed at any age. For in ovo vaccination, vaccination would be done in the last quarter of embryonal development but may be done at any time during embryonation. The vaccines according to the invention can, for example, be administered intramuscularly, subcutaneously, orally, intraocularly, intratracheally, intranasally, in ovo, in drinking water, in the form of sprays or by contact spread. Preferably, chickens are given the first vaccine in ovo or at one day of age. Subsequent vaccinations are done according to need. Breeder chickens can be vaccinated before and during the lay cycle (several inoculations).

In certain embodiments, the vaccine is administered in poultry feed.

In certain embodiments, the vaccine is administered by injection.

In certain embodiments, the vaccine is administered in ovo.

Adjuvants

Vaccines are often formulated and inoculated with various adjuvants. The adjuvants aid in attaining a more durable and higher level of immunity using small amounts of antigen or fewer doses than if the immunogen were administered alone. The mechanism of adjuvant action is complex, and may involve the stimulation of cytokine production, phagocytosis and other activities of the reticuloendothelial system as well as a delayed release and degradation of the antigen. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecylglycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin, and mutant forms of complete toxin in which mutations have been introduced into the A subunit of *E. coli* heat labile toxin or cholera toxin that attenuate its toxicity while retaining its adjuvant properties. McGhee, J. R., et al., "On vaccine development," *Sem. Hematol.*, 30:3-15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

In certain embodiments, a saponin adjuvant such as Quil A, various oil emulsion adjuvants such as water in oil or water in oil in water formulations are used.

The invention will now be illustrated by the following non-limiting Example.

Example 1

Introduction

*Clostridium perfringens* (*C. perfringens*) induced necrotic enteritis (NE) is becoming an economically significant problem for the broiler industry. The acute form of the disease leads to increased mortality in broiler flocks, which can account for high losses of up to 1% per day, reaching mortality rates up to 10-40%. In the subclinical form, fibrin deposits and other damage to the intestinal mucosa caused by *C. perfringens* (FIG. 1) leads to poor productivity (reduced growth, reduced feed efficiency) without mortality. *C. perfringens*-infected poultry also constitutes a risk for transmission to humans through the food chain. Historically, *C. perfringens* outbreaks in the broiler industry were avoided by the use of growth-promoting antimicrobials in the diet. However, concerns regarding antibiotic resistance led to restrictions on the use of antibiotics. This, coupled with high-density living conditions and the reuse of litter materials, has culminated in a resurgence of *C. perfringens* infections, estimated to cause a global economic loss of over $US2 billion annually.

*C. perfringens* is a Gram-positive anaerobic spore-forming bacterium. At least 17 exotoxins and enzymes responsible for the associated lesions and disease symptoms have been identified. *C. perfringens* strains are classified into five types (A, B, C, D and E), based on their ability to produce different combinations of four major toxins ($\alpha$, $\beta$, $\epsilon$ and $\iota$). NE and the subclinical form of *C. perfringens* infection in poultry are caused by *C. perfringens* type A strains. For many years, the chromosome-encoded alpha-toxin, a membrane active phospholipase, was considered to be the major toxin associated with NE. Alpha-toxin is composed of two domains, which are associated with phospholipase C activity (N-domain, 1-250 residues) and membrane recognition (C-domain, 251-370 residues), respectively. The C-terminal domain contributes to maintaining the active form of the toxin and mediates interactions with membrane phospholipids in a calcium-dependent manner. Individually these domains are non-toxic but immunogenic in mice resulting in the generation of antibody that reacts with the holotoxin, however, only immune responses against the C-domain provided protection against a subsequent challenge, possibly due to the blocking effects on the initial membrane-binding event. Therefore, the C-terminal domain of the alpha-toxin has been studied extensively as a vaccine against *C. perfringens* infection, delivered as a purified protein or by live attenuated bacteria. Currently the only commercially available vaccine for necrotic enteritis, Netvax®, is composed of an alpha toxoid derived from a *C. perfringens* type A strain.

Recent studies have identified a β-like toxin linked to necrotic enteritis, designated NetB toxin. It was identified in an Australian *C. perfringens* type A strain and has been proposed to be the most critical virulence factor for the development of NE in broilers. NetB is a pore-forming toxin encoded on a large conjugative plasmid (approximately 85 kb) within a 42 kilobase (kb) pathogenicity locus (NELoc-1), showing similarity to *C. perfringens* β-toxin (38% identity). Several studies have screened for the presence of the netB gene within *C. perfringens* isolates and found that the presence of netB gene is highly correlated with necrotic enteritis strains. NetB is also a protective antigen, which could provide protection against *C. perfringens* challenge, especially in combination with other immunogenic components. Results consistent with a protective role for immune responses to NetB were obtained in a study that examined serum antibody levels against *C. perfringens* alpha-toxin and NetB toxin in commercial birds from field outbreaks of NE. The results showed that the levels of serum antibodies against both alpha-toxin and NetB toxin were significantly higher in apparently healthy chickens compared to birds with clinical signs of NE, suggesting that these antitoxin antibodies may play a role in protection against NE. Their results indicate a correlation between the presence of antitoxin antibodies in the serum and protective immunity against NE. In one study, purified α-toxin C-fragment and NetB (W262A) toxoids were mixed (30 μg of each) in Quil A adjuvant and used to subcutaneously inject broiler birds 3 times, on days 3, 9 and 15. Birds injected with only one of the proteins were also included. The immunized birds were partially protected against a mild gavage challenge, but not against a more severe, in feed challenge. In some studies, hens were infected with NetB toxoid and antibodies against NetB were transferred from immunized hens to progeny, providing protection against *C. perfringens* challenge. In another study, immunization with both NetB and α-toxin toxoids using a live *Salmonella* delivery vector induced mucosal antibodies against both toxins and elicited a protective response. Strains engineered to deliver both toxoids provided significantly better protection than strains delivering each toxin alone.

In the current study, the immunogenicity of a novel PlcC-NetB fusion protein was examined in broiler birds.

Materials and Methods

Growth of *C. perfringens*. *C. perfringens* CP4 was cultured in cooked meat medium (CMM; Difco) and fluid thioglycollate medium (FTG; Difco).

Purification of PlcC, NetB and PlcC-NetB proteins. His-tagged PlcC (Zekarias, B., H. Mo, and R. Curtiss, III. 2008. Recombinant attenuated *Salmonella enterica* serovar Typhimurium expressing the carboxy-terminal domain of alpha toxin from *Clostridium perfringens* induces protective responses against necrotic enteritis in chickens. Clin Vaccine Immunol 15:805-816) and GST-NetB (Jiang, Y., H. Mo, C. Willingham, S. Wang, J. Y. Park, W. Kong, K. L. Roland, and R. Curtiss, 3rd. 2015. Protection Against Necrotic Enteritis in Broiler Chickens by Regulated Delayed Lysis *Salmonella* Vaccines. Avian diseases 59:475-485) proteins were prepared from *E. coli* as described.

A fusion protein PlcC-NetB was designed comprising the following components. The PlcC component represents aa 248-370 of alpha toxin (GenBank accession AAP15462.1) (SEQ ID NO: 3). The full-length, mature (i.e., after processing) Alpha toxin (GenBank accession AAP15462.1) is the following (SEQ ID NO: 16):

WDGKIDGTGTHAMIVTQGVSILENDMSKNEPESVRKNLEILKDNMHELQL

GSTYPDYDKNAYDLYQDHFWDPDTNNNFSKDNSWYLAYSIPDTGESQIRK

FSALARYEWQRGNYKQATFYLGEAMHYFGDIDTPYHPANVTAVDSAGHVK

FETFAEERKEQYKINTVGCKTNEDFYADILKNKDFNAWSKEYARGFAKTG

KSIYYSHASMSHSWDDWDYAAKVTLANSQKGTAGYIYRFLHDVSEGNDPS

VGNNVKELVAYISTSGEKDAGTDDYMYFGIKTKDGKTQEWEMDNPGNDFM

AGSKDTYTFKLKDENLKIDDIQNMWIRKRKYTAFPDAYKPENIKVIANGK

VVVDKDINEWISGNSTYNIK

The PlcC component, which is aa 248-370 of alpha toxin (GenBank accession AAP15462.1) (SEQ ID NO: 3) is the following:

DPSVGNNVKELVAYISTSGEKDAGTDDYMYFGIKTKDGKTQEWEMDNPGN

DEMAGSKDTYTEKLKDENLKIDDIONMWIRKRKYTAFPDAYKPENIKVIA

NGKVVVDKDINEWISGNSTYNIK

The NetB component represents amino acids 31-322 of NetB (GenBank accession ACN73257.1) (SEQ ID NO: 5). The full-length NetB (GenBank accession ACN73257.1) is the following (SEQ ID NO: 17):

MKRLKIISITLVLTSVISTSLFSTQTQVFASELNDINKIELKNLSGEIIK

ENGKEAIKYTSSDTASHKGWKATLSGTFIEDPHSDKKTALLNLEGFIPSD

-continued

KQIFGSKYYGKMKWPETYRINVKSADVNNNIKIANSIPKNTIDKKDVSNS

IGYSIGGNISVEGKTAGAGINASYNVQNTISYEQPDFRTIQRKDDANLAS

WDIKFVETKDGYNIDSYHAIYGNQLFMKSRLYNNGDKNFTDDRDLSTLIS

GGFSPNMALALTAPKNAKESVIIVEYQRFDNDYILNWETTQWRGTNKLSS

TSEYNEFMFKINWQDHKIEYYL

The NetB component, which is amino acids 31-322 of NetB (GenBank accession ACN73257.1) (SEQ ID NO: 5) is the following:

SELNDINKIELKNLSGEIIKENGKEAIKYTSSDTASHKGWKATLSGTFIE

DPHSDKKTALLNLEGFIPSDKQIFGSKYYGKMKWPETYRINVKSADVNNN

IKIANSIPKNTIDKKDVSNSIGYSIGGNISVEGKTAGAGINASYNVQNTI

SYEQPDFRTIQRKDDANLASWDIKFVETKDGYNIDSYHAIYGNQLFMKSR

LYNNGDKNFTDDRDLSTLISGGFSPNMALALTAPKNAKESVIIVEYQRFD

NDYILNWETTQWRGTNKLSSTSEYNEFMFKINWQDHKIEYYL

Figure 2:
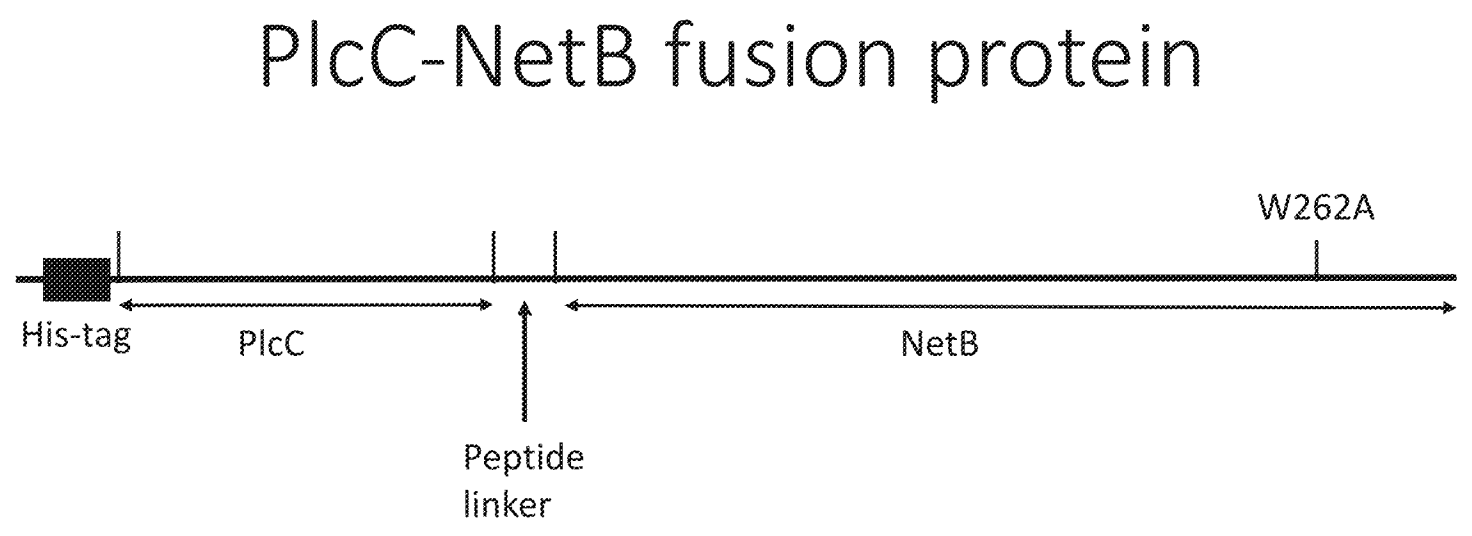

The PlcC component is linked to the NetB component by the peptide linker "GGSGGSGGPSGGSGG" (SEQ ID NO: 4), with NetB on the C-terminal side. A 6His tag (HHHHHH, SEQ ID NO:2) and linker "HHHHHHGS" (SEQ ID NO: 15) is fused to the N-terminus of PlcC (FIG. 2). Because the toxins are naturally secreted in *C. perfringens* via a processed N-terminal signal peptide, we directed the expressed fusion protein to the endoplasmic reticulum (ER) of plant cells, reasoning that correct protein folding may be enhanced by the chaperones present in the ER. In order to target the fusion protein to the ER of plant cells, the plant signal peptide from barley alpha amylase "MANKHLSLSLFLVLLGLSASLASG" (SEQ ID NO:1) is fused to the N-terminus of the 6His tag. Examination of the sequence using SignalP 4.1 (http://www.cbs.dtu.dk/services/SignalP/) and selecting "Eukaryotes" indicates that signal peptidase cleavage is likely to occur between positions 24 and 25: ASG-HH.

A plant codon-optimized coding sequence was designed to enable high expression in a tobacco relative, *Nicotiana benthamiana*. Codons were selected that are more frequently used in highly expressed genes of tobacco and *Arabidopsis* (Geyer, B. C., L. Kannan, I. Cherni, R. R. Woods, H. Soreq, and T. S. Mor. 2010. Transgenic plants as a source for the bioscavenging enzyme, human butyrylcholinesterase. Plant Biotechnol J 8:873-886). Sequences were eliminated that could specify RNA processing (splicing, polyadenylation) or destabilization. A commercial service was used for gene synthesis and cloned the fragment via XbaI at 5' and SacI at 3' into an expression vector based on a bean yellow dwarf virus replicon, pBYR2eK2M (Diamos, A. G., S. H. Rosenthal, and H. S. Mason. 2016. 5' and 3' Untranslated Regions Strongly Enhance Performance of Geminiviral Replicons in *Nicotiana benthamiana* Leaves. Front Plant Sci 7:200). The resulting construct pBYR2eK2M-6HplcCnetB was verified by DNA sequencing and transformed into the disarmed *Agrobacterium tumefaciens* strain EHA105. Transient expression in leaves We performed by *Agrobacterium*-mediated DNA delivery. Briefly, *Agrobacterium* cells were grown overnight in LB media with 50 μg/ml kanamycin and 1 μg/ml rifampicin, and then cells were collected and resuspended in 10 mM 2-(N-morpholino)ethanesulfonic acid (MES), pH 5.5 and 10 mM MgSO$_4$ to OD$_{600}$=0.2. The resulting bacterial suspensions were injected into leaves through a small puncture using a syringe without needle (Huang, Z., and H. S. Mason. 2004. Conformational analysis of hepatitis B surface antigen fusions in an *Agrobacterium*-mediated transient expression system. Plant Biotechnol J 2:241-249). The plants were cultured in a growth room under moderate light at 25° C. for 4 days before leaves were harvested and weighed.

The leaves were extracted using a blender in 3-fold mass of buffer (phosphate buffered saline pH 7.5 (PBS), 50 mM sodium ascorbate, 1 mM phenylmethylsulfonyl fluoride, 0.1% Triton X-100), and insoluble debris was removed by centrifugation (10,000×g, 4° C., 15 min). The supernatant was collected and 1 M phosphoric acid was added while stirring at 4° C. until the pH=4.8, and then 1 M Tris base was added until the supernatant reached pH=7.5. Precipitated material was removed by centrifugation (10,000×g, 4° C., 15 min), and the supernatant containing recombinant PlcC-NetB was subjected to metal affinity chromatography, using Talon® affinity resin (http://www.clontech.com). Bound protein was eluted by washing the column with 150 mM imidazole, and fractions were assayed by absorbance at 280 nm. Combined fractions with the highest protein content were dialyzed against PBS, pH 7.5, and the A$_{280}$ was measured. Protein concentration was calculated using the theoretical extinction coefficient based on the amino acid sequence of the fusion protein.

The ER-targeted construct resulted in high expression and accumulation of soluble PlcC-NetB fusion protein, which was verified by western blotting using anti-PlcC and anti-NetB antisera (data not shown). The fusion antigen was readily purified using metal affinity chromatography.

Detection of Antibody Response by Enzyme-Linked Immunosorbent Assay (ELISA)

ELISAs were performed in triplicate as described (Jiang, Y., Q. Kong, K. L. Roland, and R. Curtiss, 3rd. 2014. Membrane vesicles of *Clostridium perfringens* type A strains induce innate and adaptive immunity. International journal of medical microbiology: IJMM 304:431-443) to determine the titer of IgY r against PlcC, NetB and PlcC-NetB in chicken sera. Nunc Immunoplate Maxisorb F96 plates (Nalge Nunc, Rochester, NY) were coated overnight at 4° C. with purified proteins at 100 ng/well suspended in sodium carbonate-bicarbonate buffer (pH 9.6). The plates were blocked with Sea Block blocking buffer (Fisher). Sera from individual birds were serially diluted in 2-fold steps from an initial dilution of 1:10 in PBS, respectively. After 1 h incubation at 37° C., wells were washed three times with PBS-0.05% Tween-20. The plates were incubated with biotinylated IgY (Southern Biotech) antibodies diluted 1:10,000 for 1 h at 37° C. Then streptavidin horseradish peroxidase conjugate (Southern Biotech) was added at a 1:4,000 dilution. 2,2'-azino-bis-(3-ethylbenzthiazoline-6-sulfonic acid) (ABTS, KPL, Inc) was then added to develop the reaction. Color development (absorbance) was recorded at 405 nm using a SpectraMax M2 Multi-Mode Microplate Reader (Molecular Devices, LLC). Endpoint titers were expressed as the reciprocal log 2 values as the last sample dilution with an absorbance of 0.1 OD unit above that for the negative controls.

Chicken Experiments.

All animal experiments were conducted in compliance with the Arizona State University Institutional Animal Care and Use Committee and the Animal Welfare Act. Any chickens that had reached a pre-determined severity of clinical illness prior to the end of the experiment were humanely euthanized and necropsied. One-day-old Cornish×Rock broiler chickens were purchased from Murray McMurray Hatchery (Webster City, Iowa) and typically arrived at our facility at 2 days of age. Birds were randomly sorted and placed in pens with pine shavings on the floor. Food and water was supplied ad libitum.

Experiment 1. One week old broiler birds were vaccinated subcutaneously three times at weekly intervals with 50 µg of purified PlcC-NetB fusion protein plus 50 µg of Quil A as adjuvant. The first immunization was at 1 week of age. Control birds mock-vaccinated with Quil A only. The volume was 100 µl for all inoculations.

Experiment 2. Broiler birds were vaccinated subcutaneously three times at weekly intervals with 100 µg of purified PlcC-NetB fusion protein plus 50 µg of Quil A as adjuvant. Control birds mock-vaccinated with Quil A only. The volume was 100 µl for $1^{st}$ and $2^{nd}$ inoculations and 200 µl for $3^{rd}$ inoculation due to the lower concentration of protein in that preparation.

In Experiment 1, serum was taken one week after the final immunization and assayed for IgY antibodies against PlcC, NetB and PlcC-NetB fusion protein.

Challenge procedure. The in-feed challenge performed as described previously (Jiang, Y., H. Mo, C. Willingham, S. Wang, J. Y. Park, W. Kong, K. L. Roland, and R. Curtiss, 3rd. 2015. Protection Against Necrotic Enteritis in Broiler Chickens by Regulated Delayed Lysis *Salmonella* Vaccines. Avian diseases 59:475-485; Shojadoost, B., A. R. Vince, and J. F. Prescott. 2012. The successful experimental induction of necrotic enteritis in chickens by *Clostridium perfringens*: a critical review. Vet Res 43:74). Three weeks after the first immunization, birds were challenged in-feed for 5 days with *C. perfringens* CP4, a virulent strain isolated from a necrotic enteritis outbreak. The day after the final challenge birds were euthanized and necropsies performed. At necropsy, intestinal tracts were examined and scored for lesions typical of necrotic enteritis. The person performing the scoring was blinded to the treatment regimen each bird received. Intestinal lesions are scored as follows: 0=no gross lesions; 1=thin or friable wall or diffuse superficial but removable fibrin; 2=focal necrosis or ulceration, or non-removable fibrin deposit, 1 to 5 foci; 3=focal necrosis or ulceration, or non-removable fibrin deposit, 6 to 15 foci; 4=focal necrosis or ulceration, or non-removable fibrin deposit, 16 or more foci; 5=patches of necrosis 2 to 3 cm long; 6=diffuse necrosis typical of field cases.

Results PlcC-NetB protein production in *Nicotiana benthamiana*. A codon-optimized gene was designed (FIG. 2) for expression of PlcC-NetB in *Nicotiana benthamiana*, and it was cloned in an expression vector based on a bean yellow dwarf virus replicon (Diamos, A. G., S. H. Rosenthal, and H. S. Mason. 2016. 5' and 3' Untranslated Regions Strongly Enhance Performance of Geminiviral Replicons in *Nicotiana benthamiana* Leaves. Front Plant Sci 7:200). The system uses transient expression in leaves, with amplified DNA and greatly enhanced protein expression only four days after *Agrobacterium*-mediated DNA delivery. Because the toxins are naturally secreted in *C. perfringens* via a processed N-terminal signal peptide, the expressed fusion protein was directed to the ER of plant cells using a barley alpha-amylase signal peptide, reasoning that correct protein folding may be enhanced by the chaperones present in the ER. The construct resulted in high expression and accumulation of soluble PlcC-NetB fusion protein, which was readily purified using metal affinity chromatography, and used for a preliminary chicken immunization experiment (see below). The data indicate that the plant-made fusion protein was immunogenic.

Figure 3:
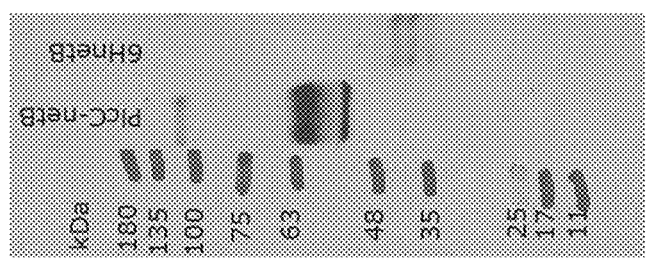
FIG. 3. Western blot of plant-made PlcC-NetB fusion and NetB proteins. Extracts of *N. benthamiana* leaf samples expressing either PlcC-NetB fusion or NetB proteins were resolved by SDS-PAGE and electro-blotted to a PVDF membrane and probed with rabbit anti-NetB serum. For NetB, 4 different forms can be observed, with the smallest at ~34 kDa (the theoretical size of unglycosylated NetB) and the largest ~46 kDa, suggesting glycosylation at all 4 potential Asn-linked sites. For PlcC-NetB fusion protein, the theoretical size of unglycosylated protein is ~49 kDa; the observed bands occur between ~52 kDa and 62 kDa, with the largest suggesting glycosylation at all 5 potential Asn-linked sites.

Evidence was observed on western blots that the PlcC-NetB accumulated in several glycosylated forms (FIG. 3). A search of the PlcC-NetB amino acid sequence for consensus Asn-linked glycosylation sites (Asn-X-Ser/Thr) showed one site in the PlcC and four sites in the NetB domain. Mapping of these sites on the 3-dimensional structures of Plc and NetB showed that they mostly occur in surface loops, and thus probably would not interfere with correct folding of the proteins or impair the antigen structure of protective epitopes. In some cases, such eukaryotic glycosylation was shown to be either neutral in effect or enhance immunogenicity of plant-made antigens (Boes, A., H. Spiegel, G. Edgue, S. Kapelski, M. Scheuermayer, R. Fendel, E. Remarque, F. Altmann, D. Maresch, A. Reimann, G. Pradel, S. Schillberg, and R. Fischer. 2015. Detailed functional characterization of glycosylated and nonglycosylated variants of malaria vaccine candidate PfAMA1 produced in *Nicotiana benthamiana* and analysis of growth inhibitory responses in rabbits. Plant Biotechnol J 13:222-234.; Joensuu, J. J., M. Kotiaho, T. H. Teeri, L. Valmu, A. M. Nuutila, K. M. Oksman-Caldentey, and V. Niklander-Teeri. 2006. Glycosylated F4 (K88) fimbrial adhesin FaeG expressed in barley endosperm induces ETEC-neutralizing antibodies in mice. Transgenic Res 15:359-373; Yuki, Y., M. Mejima, S. Kurokawa, T. Hiroiwa, Y. Takahashi, D. Tokuhara, T. Nochi, Y. Katakai, M. Kuroda, N. Takeyama, K. Kashima, M. Abe, Y. Chen, U. Nakanishi, T. Masumura, Y. Takeuchi, H. Kozuka-Hata, H. Shibata, M. Oyama, K. Tanaka, and H. Kiyono. 2013. Induction of toxin-specific neutralizing immunity by molecularly uniform rice-based oral cholera toxin B subunit vaccine without plant-associated sugar modification. Plant Biotechnol J 11:799-808). However, it is difficult to predict the effects of glycosylation on the immunogenicity of PlcC-NetB. Although the preliminary study showed it is immunogenic in chickens, it is possible that a non-glycosylated protein will be even more potent. Thus, a new expression vector was constructed that lacks the N-terminal signal sequence, which resulted in cytosolic accumulation and thus unglycosylated antigen. The glycosylated and unglycosylated antigens are used in further studies to test immunogenicity and protection in chickens.

Figures 4A, 4B, 4C:
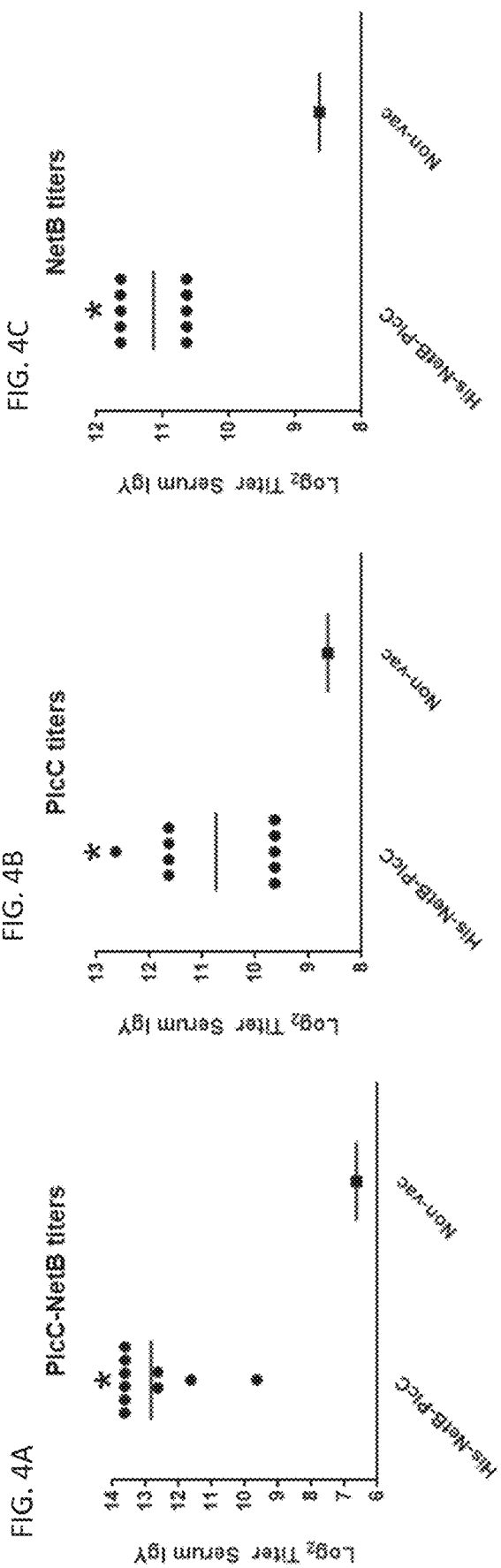
FIGS. 4A-4C. IgY serum titers from immunized and non-immunized birds in Experiment 1. A paired t-test was performed between chickens that received the fusion protein and non-vaccinated control group.
Figure 5:
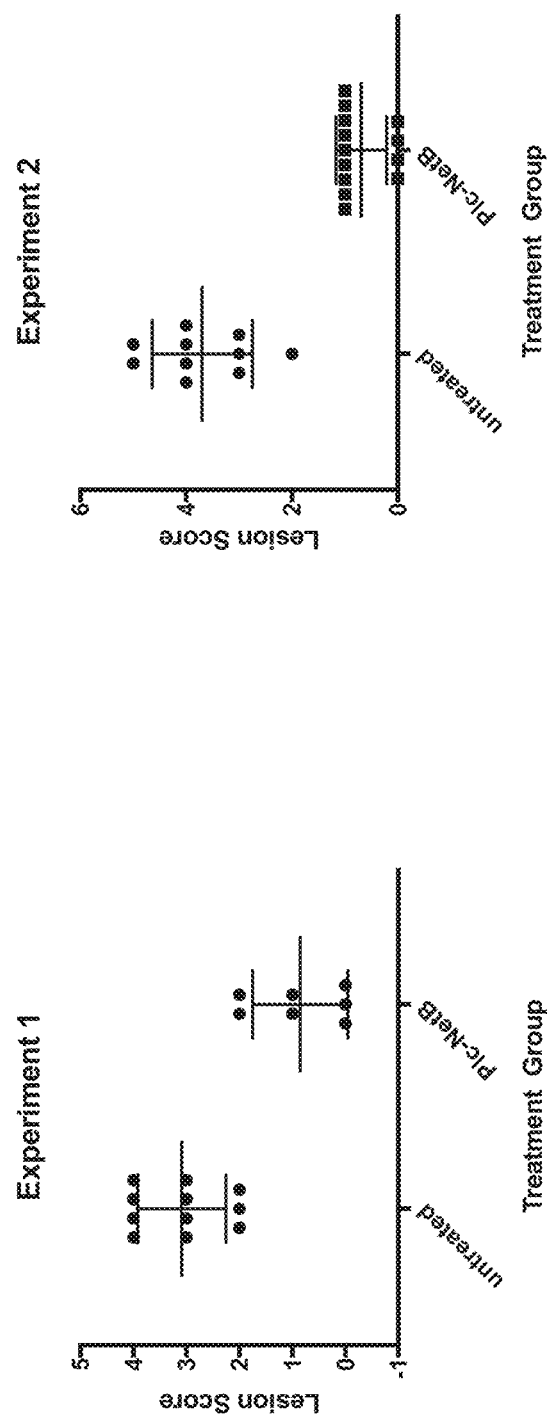
FIG. 5. Summary of lesion scores from Experiments 1 and 2.

Serum antibody responses to the PlcC-NetB fusion protein. Serum IgY responses against the PlcC-NetB protein were significantly higher in immunized birds compared to non-vaccinated controls (FIG. 4A), indicating that PlcC-NetB is highly immunogenic. However, the protein is glycosylated (FIG. 3) and some of the reacting antibodies could be against the carbohydrate moieties, which are not present in the corresponding proteins produced by *C. perfringens*. To examine the responses against the proteinaceous epitopes, PlcC and NetB proteins purified from *E. coli* were used as the coating antigen. Although the titers were somewhat lower, they remained significantly higher than titers from control animals, indicating that protein epitopes in the PlcC (FIG. 4B) and NetB (FIG. 4C) were being recognized.

Protection Against *C. perfringens* Challenge.

The results from both challenge experiments are summarized below in Table 1 and graphically in FIG. 4. The challenge in Experiment 1 was milder than in Experiment 2, based on the fact that in Experiment 1, none of the birds in the control group received a lesion score of 5. This was due to the fact that different subclones of CP4 were used in each experiment. Interestingly, the vaccinated birds in Experiment 2 had overall healthier intestinal tracts than in Experiment 1. In Experiment 1 in which the birds received three doses of 50 µg of PlcC-NetB, after challenge, the intestines of most of the vaccinated birds displayed friability, even in the absence of fibrin. In Experiment 2, where the birds received three doses of 100 µg of PlcC-NetB, there was little friability and only scattered, removable fibrin. This is remarkable considering that the challenge was stronger in Experiment 2. These results demonstrate that the PlcC-NetB protein is highly immunogenic and protective against an in-feed challenge with a highly virulent *C. perfringens* strain.

TABLE 1

Lesion scores in immunized and non-immunized birds

| Group | Lesion Score | | | | | | | Average Lesion Score |
|---|---|---|---|---|---|---|---|---|
| | 0 | 1 | 2 | 3 | 4 | 5 | 6 | |
| Exp. 1 | | | | | | | | |
| PlcC-NetB | 3 | 2 | 2 | 0 | 0 | 0 | 0 | 0.9* |
| Mock | 0 | 0 | 3 | 4 | 3 | 0 | 0 | 3.0 |
| Exp. 2 | | | | | | | | |
| PlcC-NetB | 4 | 9 | 0 | 0 | 0 | 0 | 0 | 0.7* |
| Mock | 0 | 0 | 1 | 3 | 4 | 2 | 0 | 3.7 |

*Different from controls, P = 0.0004 by Mann-Whitney test
**Different from controls, P < 0.001 by Mann-Whitney test
Experiment 1: n = 7, PlcC-NetB group; n = 10, mock vaccinated group
Experiment 2: n = 13, PlcC-NetB group; n = 10, mock vaccinated group Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of protecting an avian species from *C. perfringens* infection comprising administering a vaccine comprising an antigenic protein, wherein the antigenic protein comprises a PlcC protein unit that is operably linked to a peptide linker that is operably linked to a NetB protein unit, wherein the PlcC protein unit, the peptide linker and the NetB protein unit each have an N-terminus and a C-terminus, wherein the C-terminus of the PlcC protein unit is linked to the N-terminus of the peptide linker, wherein the C-terminus of the peptide linker is operably linked to the N-terminus of the NetB protein unit, and wherein the peptide linker has at least 95% sequence identity to SEQ ID NO: 4.

2. The method of claim 1, wherein the PlcC protein unit has at least 95% sequence identity to SEQ ID NO: 3.

3. The method of claim 1, wherein the PlcC protein unit has 100% sequence identity to SEQ ID NO: 3.

4. The method of claim 1, wherein the NetB protein unit has at least 95% sequence identity to SEQ ID NO: 5.

5. The method of claim 4, wherein the NetB protein unit has one or more amino acid substitutions at Y191A, R200A, W257A and W262A, S254L, R230Q or W287R of SEQ ID NO: 5.

6. The method of claim 1, wherein the antigenic protein further comprises a 6Hist tag (SEQ ID NO: 2) having an N-terminus and a C-terminus, wherein the C-terminus of the 6Hist tag is operably linked to the N-terminus of the PlcC protein unit.

7. The method of claim 1, wherein the antigenic protein further comprises a plant signal peptide having an N-terminus and a C-terminus, wherein the C-terminus of the plant signal peptide is operably linked to the N-terminus of the 6Hist tag, wherein the plant signal peptide has at least 95% sequence identity to SEQ ID NO: 1.

8. The method of claim 1, wherein the vaccine is administered in poultry feed, is administered by injection, or is administered in ovo.

* * * * *

```
                              SEQUENCE LISTING

Sequence total quantity: 17
SEQ ID NO: 1            moltype = AA  length = 24
FEATURE                 Location/Qualifiers
REGION                  1..24
                        note = Description of Unknown: Plant signal peptide
source                  1..24
                        mol_type = protein
                        organism = unidentified
SEQUENCE: 1
MANKHLSLSL FLVLLGLSAS LASG                                              24

SEQ ID NO: 2            moltype = AA  length = 6
FEATURE                 Location/Qualifiers
REGION                  1..6
                        note = Description of Artificial Sequence: Synthetic 6xHis
                         tag
source                  1..6
                        mol_type = protein
                        organism = synthetic construct
SEQUENCE: 2
HHHHHH                                                                  6

SEQ ID NO: 3            moltype = AA  length = 123
FEATURE                 Location/Qualifiers
source                  1..123
                        mol_type = protein
                        organism = Clostridium perfringens
SEQUENCE: 3
DPSVGNNVKE LVAYISTSGE KDAGTDDYMY FGIKTKDGKT QEWEMDNPGN DFMAGSKDTY        60
TFKLKDENLK IDDIQNMWIR KRKYTAFPDA YKPENIKVIA NGKVVVDKDI NEWISGNSTY       120
NIK                                                                    123

SEQ ID NO: 4            moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 4
GGSGGSGGPS GGSGG                                                        15

SEQ ID NO: 5            moltype = AA  length = 292
FEATURE                 Location/Qualifiers
source                  1..292
                        mol_type = protein
                        organism = Clostridium perfringens
SEQUENCE: 5
SELNDINKIE LKNLSGEIIK ENGKEAIKYT SSDTASHKGW KATLSGTFIE DPHSDKKTAL        60
LNLEGFIPSD KQIFGSKYYG KMKWPETYRI NVKSADVNNN IKIANSIPKN TIDKKDVSNS       120
IGYSIGGNIS VEGKTAGAGI NASYNVQNTI SYEQPDFRTI QRKDDANLAS WDIKFVETKD       180
GYNIDSYHAI YGNQLFMKSR LYNNGDKNFT DDRDLSTLIS GGFSPNMALA LTAPKNAKES       240
VIIVEYQRFD NDYILNWETT QWRGTNKLSS TSEYNEFMFK INWQDHKIEY YL               292

SEQ ID NO: 6            moltype = DNA  length = 1389
FEATURE                 Location/Qualifiers
misc_feature            1..1389
                        note = Description of Artificial Sequence: Synthetic
                         polynucleotide
source                  1..1389
                        mol_type = other DNA
                        organism = synthetic construct
SEQUENCE: 6
atggctaaca agcacctctc attgtctctc ttccttgtgc tccttggtct ttctgcttct        60
cttgcttctg gtcaccatca ccatcatcac ggatccgacc catccgtggg aaacaacgtt       120
aaggagcttg tggcttacat ctccacttct ggagagaagg acgctggaac cgacgattac       180
atgtacttcg gtatcaagac caaggatgga aagactcaag aatgggagat ggacaatcca       240
ggtaacgact tcatggctgg tagcaaggat acttacactt tcaagttgaa agacgagaac       300
cttaagatcg acgacatcca gaacatgtgg attaggaaac gtaagtacac cgccttccca       360
gacgcttaca agcctgagaa catcaaggtt atcgtaacg gaaaggtggt tgttgacaag        420
```

```
gatatcaacg agtggatttc tggaaactcc acttacaaca tcaaaggagg ttctggtgga    480
tcaggaggtc catctggagg ttctggagga tccgagctta acgacatcaa caagattgag    540
cttaagaacc tctccggaga gatcatcaag gagaacggta aggaggctat caagtacact    600
tcttccgaca ccgcttccca caagggatgg aaggccactc tttctggaac cttcatcgaa    660
gaccctcatt ctgacaagaa gactgctttg cttaaccttg aaggattcat cccatctgac    720
aaacagatct tcggatctaa gtactacgga aagatgaagt ggcctgagac ttacaggatc    780
aacgtgaaga gcgctgacgt taacaacaac atcaagatcg ccaactctat tccgaagaac    840
actatcgaca gaaggacgt gtccaattct atcggttact ccatcggagg taacatctct     900
gttgagggta agactgctgg tgctggaatc aacgcttctt acaacgttca gaacactatc    960
tcctatgagc aacctgactt cagaaccatt cagaggaagg acgatgctaa ccttgcatcc   1020
tgggacatca aattcgttga gactaaggac ggatacaaca tcgactccta ccatgctatc   1080
tatgcaaacc agctcttcat gaagagcaga ttgtacaaca atggtgacaa gaacttcacc   1140
gacgataggg acctctccac cttgatctct ggtggattct ctccaaacat ggctcttgcc   1200
ttgaccgctc ctaagaacgc taaggagtca gtgatcatcg ttgaatacca gaggttcgac   1260
aacgactata tccttaactg ggagactact caagctagag gaactaacaa gctttcttca   1320
acctccgagt acaacgagtt tatgttcaag atcaactggc aggaccacaa gatcgaatac   1380
tatctttaa                                                           1389

SEQ ID NO: 7          moltype = DNA   length = 1386
FEATURE               Location/Qualifiers
misc_feature          1..1386
                      note = Description of Artificial Sequence: Synthetic
                       polynucleotide
source                1..1386
                      mol_type = other DNA
                      organism = synthetic construct
SEQUENCE: 7
atggctaaca agcacctctc attgtctctc ttccttgtgc tccttggtct ttctgcttct     60
cttgcttctg gtcaccatca ccatcatcac ggatccgacc catccgtggg aaacaacgtt    120
aaggagcttg tggcttacat ctccacttct ggagagaagg acgctgaac cgacgattac    180
atgtacttcg gtatcaagac caaggatgga aagactcaag aatgggagat ggacaatcca    240
ggtaacgact tcatgctgg tagcaaggat acttacactt tcaagttgaa agacgagaac    300
cttaagatca cgacatcca gaacatgtgg attaggaaac gtaagtacac cgccttccca    360
gacgcttaca agcctgagaa catcaaggtt atcgctcaag gaaaggtggt tgttgacaag    420
gatatcaacg agtggatttc tggaaactcc acttacaaca tcaaaggagg ttctggtgga    480
tcaggaggtc catctggagg ttctggagga tccgagctta acgacatcaa caagattgag    540
cttaagaacc tctccggaga gatcatcaag gagaacggta aggaggctat caagtacact    600
tcttccgaca ccgcttccca caagggatgg aaggccactc tttctggaac cttcatcgaa    660
gaccctcatt ctgacaagaa gactgctttg cttaaccttg aaggattcat cccatctgac    720
aaacagatct tcggatctaa gtactacgga aagatgaagt ggcctgagac ttacaggatc    780
aacgtgaaga gcgctgacgt taacaacaac atcaagatcg ccaactctat tccgaagaac    840
actatcgaca gaaggacgt gtccaattct atcggttact ccatcggagg taacatctct     900
gttgagggta agactgctgg tgctggaatc aacgcttctt acaacgttca gaacactatc    960
tcctatgagc aacctgactt cagaaccatt cagaggaagg acgatgctaa ccttgcatcc   1020
tgggacatca aattcgttga gactaaggac ggatacaaca tcgactccta ccatgctatc   1080
tatgcaaacc agctcttcat gaagagcaga ttgtacaaca atggtgacaa gaacttcacc   1140
gacgataggg acctctccac cttgatctct ggtggattct ctccaaacat ggctcttgcc   1200
ttgaccgctc ctaagaacgc taaggagtca gtgatcatcg ttgaatacca gaggttcgac   1260
aacgactata tccttaactg ggagactact caagctagcg gaactaacaa gctttcttca   1320
acctccgagt acaacgagtt tatgttcaag atcaactggc aggaccacaa gatcgaatac   1380
tatctt                                                              1386

SEQ ID NO: 8          moltype = DNA   length = 1320
FEATURE               Location/Qualifiers
misc_feature          1..1320
                      note = Description of Artificial Sequence: Synthetic
                       polynucleotide
source                1..1320
                      mol_type = other DNA
                      organism = synthetic construct
SEQUENCE: 8
atggctcacc atcaccatca tcacggatcc gacccatccg tgggaaacaa cgttaaggag     60
cttgtggctt acatctccac ttctggagag aaggacgctg aaccgacga ttacatgtac    120
ttcggtatca agaccaagga tggaaagact caagaatggg agatggacaa tccaggtaac    180
gacttcatgg ctggtagcaa ggatacttac actttcaagt tgaaagacga gaaccttaag    240
atcgacgaca tccagaacat gtggattagg aaacgtaagt acaccgcctt cccagacgct    300
tacaagcctg agaacatcaa ggttatcgct aacgaaaggt ggttgttga aggatatc     360
aacgagtgga tttctggaaa ctccacttac aacatcaaag gaggttctgg tggatcagga    420
ggtccatctg gaggttctgg aggatccgag cttaacgaca tcaacaagat tgagcttaag    480
aacctctccg gagagatcat caaggagaac ggtaaggagg ctatcaagta cacttcttcc    540
gacaccgctt cccacaaggg atggaaggcc actctttctg gaaccttcat cgagaccct    600
cattctgaca gaagactgc tttgcttaac cttgaaggat tcatcccatc tgacaaacag    660
atcttcggat ctaagtacta cggaaagatg aagtggcctg agacttacag gatcaacgtg    720
aagagcgctg acgttaacaa caacatcaag atcgccaact ctattccgaa gaacactatc    780
gacagaagg acgtgtccaa ttctatcggt tactccatcg gaggtaacat ctctgttgag    840
ggtaagactg ctggtgctgg aatcaacgct tcttacaacg ttcagaacac tatctcctat    900
gagcaacctg acttcagaac cattcagagg aaggacgatg ctaaccttgc atcctgggac   960
atcaaattcg ttgagactaa ggacggatac aacatcgact cctaccatgc tatctatggc   1020
aaccagctct tcatgaagag cagattgtac aacaatggtg acaagaactt caccgacgat   1080
```

```
agggacctct ccaccttgat ctctggtgga ttctctccaa acatggctct tgccttgacc  1140
gctcctaaga acgctaagga gtcagtgatc atcgttgaat accagaggtt cgacaacgac  1200
tatatcctta actgggagac tactcaagct agaggaacta acaagctttc ttcaacctcc  1260
gagtacaacg agtttatgtt caagatcaac tggcaggacc acaagatcga atactatctt  1320
```

```
SEQ ID NO: 9              moltype = DNA   length = 465
FEATURE                   Location/Qualifiers
misc_feature              1..465
                          note = Description of Artificial Sequence: Synthetic
                            polynucleotide
source                    1..465
                          mol_type = other DNA
                          organism = synthetic construct
SEQUENCE: 9
atggctaaca agcacctctc attgtctctc ttccttgtgc tccttggtct ttctgcttct   60
cttgcttctg gtcaccatca ccatcatcac ggatccgacc catccgtggg aaacaacgtt  120
aaggagcttg tggcttacat ctccacttct ggagagaagg acgctggaac cgacgattac  180
atgtacttcg gtatcaagac caaggatgga aagactcaag aatgggagat ggacaatcca  240
ggtaacgact tcatggctgg tagcaaggat acttacactt tcaagttgaa agacgagaac  300
cttaagatcg acgacatcca gaacatgtgg attaggaaac gtaagtacac cgccttccca  360
gacgcttaca agcctgagaa catcaaggtt atcgctaacg gaaaggtggt tgttgacaag  420
gatatcaacg agtggatttc tggaaactcc acttacaaca tcaaa                  465

SEQ ID NO: 10             moltype = DNA   length = 399
FEATURE                   Location/Qualifiers
misc_feature              1..399
                          note = Description of Artificial Sequence: Synthetic
                            polynucleotide
source                    1..399
                          mol_type = other DNA
                          organism = synthetic construct
SEQUENCE: 10
atggctcacc atcaccatca tcacggatcc gacccatccg tgggaaacaa cgttaaggag   60
cttgtggctt acatctccac ttctggagag aaggacgctg gaaccgacga ttacatgtac  120
ttcggtatca agaccaagga tggaaagact caagaatgga gatggacaat tccaggtaac  180
gacttcatgg ctggtagcaa ggatacttac actttcaagt tgaaagacga gaaccttaag  240
atcgacgaca tccagaacat gtggattagg aaacgtaagt acaccgcctt cccagacgct  300
tacaagcctg agaacatcaa ggttatcgct aacgaaaggt ggttgttga caaggatatc  360
aacgagtgga tttctggaaa ctccacttac aacatcaaa                         399

SEQ ID NO: 11             moltype = DNA   length = 969
FEATURE                   Location/Qualifiers
misc_feature              1..969
                          note = Description of Artificial Sequence: Synthetic
                            polynucleotide
source                    1..969
                          mol_type = other DNA
                          organism = synthetic construct
SEQUENCE: 11
atggctaaca agcacctctc attgtctctc ttccttgtgc tccttggtct ttctgcttct   60
cttgcttctg gtcaccatca ccatcatcac ggatccgacc ttaacgacat caacaagatt  120
gagcttaaga acctctccgg agagatcatc aaggagaacg gtaaggaggc tatcaagtac  180
acttcttccg acaccgcttc ccacaaggga tggaaggcca ctctttctgg aaccttcatc  240
gaagaccctc attctgacaa gaagactgct tgcttaaccc ttgaaggatt catcccatct  300
gacaaactga tcttcggatc taagtactac ggaaagtaca agtggcctga gacttacagg  360
atcaacgtga gagcgctgaa cgttaacaac aacatcaaga tcgccaactc tattccgaag  420
aacactatcg acaagaagga cgtgtccaat tctatcggtt actccatcgg aggtaacatc  480
tctgttgagg gtaagactgc tggtgctgga atcaacgctt cttacaacgt tcagaacact  540
atctcctatg agcaacctga cttcagaacc attcagagga aggacgatgc taaccttgca  600
tcctgggaca tcaaattcgt tgagactaag gacggataca acatcgactc ctaccatgct  660
atctatggca accagctctt catgaagagc agattgtaca acaatggtga acgaacttc   720
accgacgata gggacctctc cacccttgat ctctggtgga tctctccaaa catggctctt  780
gccttgaccc tcctaagaa cgctaaggag tcagtgatca tcgttaata ccagaggttc   840
gacaacgact atatccttaa ctgggagact actcaagcta gaggaactaa caagctttct  900
tcaacctccg agtacaacga gtttatgttc aagatcaact ggcaggacca caagatcgaa  960
tactatctt                                                          969

SEQ ID NO: 12             moltype = DNA   length = 903
FEATURE                   Location/Qualifiers
misc_feature              1..903
                          note = Description of Artificial Sequence: Synthetic
                            polynucleotide
source                    1..903
                          mol_type = other DNA
                          organism = synthetic construct
SEQUENCE: 12
atggctcacc atcaccatca tcacggatcc gagcttaacg acatcaacaa gattgagctt   60
aagaaccctct ccgagagat catcaaggag aacggtaagg aggctatcaa gtacacttct  120
tccgacaccg cttcccacaa gggatggaag gccactcttt ctggaacctt catcgaagac  180
```

```
cctcattctg acaagaagac tgctttgctt aaccttgaag gattcatccc atctgacaaa    240
cagatcttcg gatctaagta ctacggaaag atgaagtggc ctgagactta caggatcaac    300
gtgaagagcg ctgacgttaa caacaacatc aagatcgcca actctattcc gaagaacact    360
atcgacaaga aggacgtgtc caattctatc ggttactcca tcggaggtaa catctctgtt    420
gagggtaaga ctgctggtgc tggaaatcaa gcttcttaca acgttcagaa cactatctcc    480
tatgagcaac ctgacttcag aaccattcag aggaaggacg atgctaacct tgcatcctgg    540
gacatcaaat tcgttgagac taaggacgga tacaacatcg actcctacca tgctatctat    600
ggcaaccagc tcttcatgaa gagcagattg tacaacaatg gtgacaagaa cttcaccgac    660
gatagggacc tctccacctt gatctctggt ggattctctc caaacatggc tcttgccttg    720
accgctccta agaacgctaa ggagtcagtg atcatcgttg aataccagag gttcgacaac    780
gactatatcc ttaactggga gactactcaa gctagaggaa ctaacaagct tcttcaacc     840
tccgagtaca acgagtttat gttcaagatc aactggcagg accacaagat cgaatactat    900
ctt                                                                  903

SEQ ID NO: 13         moltype = AA   length = 462
FEATURE               Location/Qualifiers
REGION                1..462
                      note = Description of Artificial Sequence: Synthetic
                      polypeptide
source                1..462
                      mol_type = protein
                      organism = synthetic construct
SEQUENCE: 13
MANKHLSLSL FLVLLGLSAS LASGHHHHHH GSDPSVGNNV KELVAYISTS GEKDAGTDDY     60
MYFGIKTKDG KTQEWEMDNP GNDFMAGSKD TYTFKLKDEN LKIDDIQNMW IRKRKYTAFP    120
DAYKPENIKV IANGKVVVDK DINEWISGNS TYNIKGGSGG SGGPSGGSGG SELNDINKIE    180
LKNLSGEIIK ENGKEAIKYT SSDTASHKGW KATLSGTFIE DPHSDKKTAL LNLEGFIPSD    240
KQIFGSKYYG KMKWPETYRI NVKSADVNNN IKIANSIPKN TIDKKDVSNS IGYSIGGNIS    300
VEGKTAGAGI NASYNVQNTI SYEQPDFRTI QRKDDANLAS WDIKFVETKD GYNIDSYHAI    360
YGNQLFMKSR LYNNGDKNFT DDRDLSTLIS GGFSPNMALA LTAPKNAKES VIIVEYQRFD    420
NDYILNWETT QARGTNKLSS TSEYNEFMFK INWQDHKIEY YL                       462

SEQ ID NO: 14         moltype = DNA   length = 14282
FEATURE               Location/Qualifiers
misc_feature          1..14282
                      note = Description of Artificial Sequence: Synthetic
                      polynucleotide
source                1..14282
                      mol_type = other DNA
                      organism = synthetic construct
SEQUENCE: 14
cgatcggtcg attcatagaa gattagattt ttcatagtat ttttttaaag taaaccttta     60
actacggtta ggacacttt aagttaaatt taatttgaac ccttaaatta attttaaaa     120
tagataaata tcaatcatcc tgatatgctt ttgaaaaaat gaatgagaaa gatgattcaa    180
ttaaggccac attttaatca tgactaaaat aatatacagt ataatttcat atatatttgc    240
tttaaaaaaa aattgacaat ccattcgttt ctagcaataa atttcttcaa ccacaaatat    300
attaaagata actacggcat agaaacaaaa atctatgaag attttttgta tacttcatat    360
gaaattaaaa aaaacttcat tgaacatcaa aataataata ataatcataa actcctcaat    420
atttatattc ctagcttctt gaattaaatt gtttacatat tcaacgatgt aaaaaaattat    480
ttctctatct attttcctta tatcatgcat ggtttcacat atatcaaagg ataaaagcaa    540
tctatgtaaa ttatctcact ttattaagtt ttctatctga attattgaga acgtagattt    600
cttttttgcac tatcccccaa taattagcaa aacacaccta gactagattt gttttgctaa    660
cccaattgat attaattata tatgattaat atttatatgt atatgaaatt ggttaataaa    720
atgcatctgg ttcatcaaag aattataaag acacgtgaca ttcatttagg ataagaaata    780
tggatgatct cttttctctta ttcagataat tagtaattac acataacaca caactttgat    840
gcccacatta tagtgattag catgtcacta tgtgtgcatc ctttttattc atacattaat    900
taacttggcc aatccagaag atggacaagt ctagggtcac attgcagggt actctagctt    960
actcgccttc ttttttcgaag gtttgagtac cttcagggca tcctcttgat acattacttt   1020
ccacttcgat tgggcaagc tgtagcagtt cttgcttaga ccgaattgcc atctcacaga    1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctggagt   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgttgg   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg gtggggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctggcaatg gaatccgagg aggtttccgg   1860
atattcccct ttgttgaaaa gtctcaattg ccctttggtc ttctgagact gtatctttga   1920
tattttggga gtagacaagt gtgtcgtgct ccacatgtc ttggcaattc gttcttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttcctta gcagcccttg   2160
cgccctgagt gcttgcggca gcgtgaagct ggcgcgccgc tctagcagaa ggcatggtgt   2220
tgtgactccg agggggttgcc tcaaactcta tcttataacc ggcgtggagg catggaggca   2280
```

```
agggcatttt ggtaatttaa gtagttagtg gaaaatgacg tcatttactt aaagacgaag  2340
tcttgcgaca aggggggccc acgccgaatt ttaatattac cggcgtggcc ccaccttatc  2400
gcgagtgctt tagcacgagc ggtccagatt taaagtagaa aagttcccgc ccactagggt  2460
taaaggtgtt cacactataa aagcatatac gatgtgatgg tatttgataa agcgtatatt  2520
gtatcaggta tttccgtcgg atacgaatta ttcgtacgac cctcctgcag gtcaacatgg  2580
tggagcacga cacacttgtc tactccaaaa atatcaaaga tacagtctca gaagaccaaa  2640
gggcaattga gacttttcaa caaagggtaa tatccggaaa cctcctcgga ttccattgcc  2700
cagctatctg tcactttatt gtgaagatag tggaaaagga aggtggctcc tacaaatgcc  2760
atcattgcga taaaggaaag gccatcgttg aagatgcctc tgccgacagt ggtcccaaag  2820
atggaccccc acccacgagg agcatcgtgg aaaaagaaga cgttccaacc acgtcttcaa  2880
agcaagtgga ttgatgtgat aacatggtgg agcacgacac acttgtctac tccaaaaata  2940
tcaaagatac agtctcagaa gaccaaaggg caattgagac ttttcaacaa agggtaatat  3000
ccggaaacct cctcggattc cattgccag ctatctgtca ctttattgtg aagatagtgg  3060
aaaaggaagg tggctcctac aaatgccatc attgcgataa aggaaaggcc atcgttgaag  3120
atgcctctgc cgacagtggt cccaaagatg gaccccacc cacgaggagc atcgtggaaa  3180
aagaagacgt tccaaccacg tcttcaaagc aagtggattg atgtgatatc tccactgacg  3240
taagggatga cgcacaatcc cactatcctt cgcaagaccc ttcctctata taggaagttt  3300
catttcattt ggagaggacc tcgagaaaca aacaaaatca acaaatatag aaaatatcgc  3360
atttccaatt ctttgaaatt tctgcaacat ctagaacaat ggctaacaag cacctctcat  3420
tgtctctctt ccttgtgctc cttggtcttt ctgcttctct tgcttctggt caccatcacc  3480
atcatcacgg atccgaccca tccgtgggaa acaacgttaa ggagcttgtg cttacatct   3540
ccacttctgg agagaaggac gctggaaccg acgattacat gtacttcggt atcaagacca  3600
aggatggaaa gactcaagaa tgggagatgg acaatccagg taacgacttc atggctggta  3660
gcaaggatac ttacactttc aagttgaaag acgagaacct taagatcgac gacatccaga  3720
acatgtggat taggaaacgt aagtacaccg ccttcccaga cgcttacaag cctgagaaca  3780
tcaaggttat cgctaacgga aaggtggttg tgacaagga tatcaacgag tggatttctg  3840
gaaactccac ttcaacatc aaaggaggtt ctggtggatc aggaggtcca tctgagggtt  3900
ctggaggatc cgagcttaac gacatcaaca agattgagct taagaacctc tccggagaga  3960
tcatcaagga gaacggtaag gaggctatca agtacacttc ttccgacacc gcttcccaca  4020
agggatggaa ggccactctt tctgaacct tcatcgaaga ccctcattct gacaagaaga  4080
ctgctttgct taaccttgaa ggattcatcc catctgacaa acagatcttc ggatctaagt  4140
actacggaaa gatgaagtgg cctgagactt acaggatcaa cgtgaagagc gctgacgtta  4200
acaacaacat caagatcgcc aactctattc gaagaacac tatcgacaag aaggacgtgt  4260
ccaattctat cggttactcc atcggaggta acatctctgt tgagggtaag actgctggtg  4320
ctggaatcaa cgcttcttac aacgttcaga cactatctc ctatgagcaa cctgacttca  4380
gaaccattca gaggaaggac gatgctaacc ttgcatcctg ggacatcaaa ttcgttgaga  4440
ctaaggacgg atacaacatc gactcctacc atgctatcta tggcaaccag ctcttcatga  4500
agagcagatt gtacaacaat ggtgacaaga acttcaccga cgataggggac ctctccaacct  4560
tgatctctgg tggattctct ccaaacatgg ctcttgcctt gaccgctcct aagaacgcta  4620
aggagtcagt gatcatcgtt gaataccaga ggttcgacaa cgactatatc cttaactggg  4680
agactactca agctagagga actaacagc tttcttcaac ctccgagtac aacgagttta  4740
tgttcaagat caactggcag gaccacaaga tcgaatacta tcttttaagag ctcgaagtga  4800
catcacaaag ttgaaggtaa taaagccaaa ttaattaaga cattccata atgatgtcaa  4860
gaatgcaaag caaattgcat aactgccttt atgcaaaaca ttaatataat ataaattata  4920
aagaactgcg ctctctgctt cttatttct tagcttcatt tattagtcac tagctgttca  4980
gaattttcag tatcttttga tattactaag aacctaatca cacaatgtat attcttatgc  5040
aggaaaagca gaatgctgag ctaaaagaaa ggcttttcc attttcgaga gacaatgaga  5100
aaagaagaag aagaagaaga agaagaagaa gaagaaaaga gtaaataata aagcccaca   5160
ggaggcgaag ttcttgtagc tccatgttat ctaagttatt gatattgttt gccctatatt  5220
ttatttctgt cattgtgtat gttttgttca gtttcgatct ccttgcaaaa tgcagagatt  5280
atgagatgaa taaactaagt tatattatta tacgtgttaa tattctcctc ctctctctag  5340
ctagcctttt gttttctctt tttcttattt gattttcttt aaatcaatcc atttttaggag  5400
agggccaggg agtgatccag caaaacatga agattagaag aaacttccct ctttttttc   5460
ctgaaaacaa tttaacgtcg agatttatct cttttttgtaa tggaatcatt tctacagtta  5520
tgacgaattc tcgattaaaa atcccaatta tatttggtct aatttgattt ggtattgagt  5580
aaaacaaatt cgaaccaaac caaaatataa atatatagtt tttatatata tgcctttaag  5640
acttttttata gaattttctt taaaaaatat ctagaaatat ttgcgactct tctggcatgt  5700
aatatttcgt taaatatgaa gtgctccatt tttattaact ttaaataatt ggttgtacga  5760
tcacttttctt atcaagtgtt actaaaatgc gtcaatctct ttgttcttcc atattcatat  5820
gtcaaaatct atcaaaattc ttatatatct ttttcgaatt tgaagtgaaa tttcgataat  5880
ttaaaattaa atagaacata tcattattta ggtatcatat tgattttat acttaattac   5940
taaatttggt taactttgaa agtgtacatc aacgaaaaat tagtcaaacg actaaaataa  6000
ataaatatca tgtgttatta agaaaattct cctataagaa tatttaata gatcatatgt  6060
ttgtaaaaaa aattaatttt tactaacaca tatatttact tatcaaaaat ttgacaaagt  6120
aagattaaaa taatattcat ctaacaaaaa aaaaccaga aaatgctgaa acccggcaa    6180
aaccgaacca atccaaaccg atatagttgg tttggtttga ttttgatata aaccgaacca  6240
actcggtcca tttgcacccc taatcataat agctttaata tttcaagata ttattaagtt  6300
aacgttgtca atatcctgga aattttgcaa aatgaatcaa gcctatatgg ctgtaatatg  6360
aatttaaaag cagctcgatg tggtggtaat atgtaattta cttgattcta aaaaaatatc  6420
ccaagtatta ataatttctg ctaggaagaa ggttagctac gatttacagc aaagccagaa  6480
tacaagaaac cataaagtga ttgaagctcg aaatatacga aggaacaaat attttaaaa   6540
aaatacgcaa tgacttggaa caaaagaaag tgatatattt tttgttctta aacaagcatc  6600
ccctctaaag aatggcagtt ttcctttgca tgtaactatt atgctcctt cgttacaaaa  6660
attttgacta ctattggga acttcttctg aaatatttgg taccgagtgt acttcaagtc  6720
agttggaaat caataaaatg attattttat gaatatattt cattgtgcaa gtagatagaa  6780
attacatatg ttacataaca cacgaaataa acaaaaaaac acaatccaaa acaaacaccc  6840
caaacaaaat aacactatat atatcctcgt atgaggagag gcacgttcag tgactcgacg  6900
attccgagc aaaaaaagtc tcccgtcac acatatagtg ggtgacgcaa ttatcttcaa   6960
agtaatcctt ctgttgactt gtcattgata acatccagtc ttcgtcagga ttgcaaagaa  7020
```

```
ttatagaagg gatcccacct tttattttct tcttttttcc atatttaggg ttgacagtga   7080
aatcagactg gcaacctatt aattgcttcc acaatgggac gaacttgaag gggatgtcgt   7140
cgatgatatt ataggtggcg tgttcatcgt agttggtgaa gtcgatggtc ccgttccagt   7200
agttgtgtcg cccgagactt ctagcccagg tggtctttcc ggtacgagtt ggtccgcaga   7260
tgtagaggct ggggtgtctg accccagtcc ttccctcatc ctggttagat cggccatcca   7320
ctcaaggtca gattgtgctt gatcgtagga gacaggatgt atgaaagtgt aggcatcgat   7380
gcttacatga tataggtgcg tctctctcca gttgtgcaga tcttcgtggc agcggagatc   7440
tgattctgtg aagggcgaca cgtactgctc aggttgtgga ggaaataatt tgttggctga   7500
atattccagc cattgaagct ttgttgccca ttcatgaggg aactcttctt tgatcatgtc   7560
aagatactcc tccttagacg ttgcagtctg gataatagtt cgccatcgtg cgtcagattt   7620
gcgaggagac accttatgat ctcggaaatc tcctctggtt ttaatatctc cgtcctttga   7680
tatgtaatca aggacttgtt tagagtttct agctggctgg atattagggt gatttccttc   7740
aaaatcgaaa aaagaaggat ccctaataca aggtttttta tcaagctgga taagagcatg   7800
atagtgggta gtgccatctt gatgaagctc agaagcaaca ccaaggaaga aaataagaaa   7860
aggtgtgagt ttctcccaga gaaactggaa taaatcatct ctttgagatg agcacttggg   7920
gtaggtaagg aaaacatatt tagattggag tctgaagttc ttgctagcag aaggcatgtt   7980
gttgtgactc cgagggggtg cctcaaactc tatcttataa ccggcgtgga ggcatggagg   8040
caaggggcatt ttggtaattt aagtagttag tggaaaatga cgtcatttac ttaaagacga   8100
agtcttgcga caaggggggc ccacgccgaa ttttaatatt accggcgtgg ccccaccta    8160
tcgcgagtgc tttagcacga gcggtccaga ttttaaagtag aaaagttccc gcccactagg   8220
gttaaaggtg ttcacactat aaaagcatat acgatgtgat ggtatttgat ggagcgtata   8280
ttgtatcagg tatttccgtc ggatacgaat tattcgtacg gccggaccgg tccccctagg   8340
cggccaattc gagatcggcc gcggctgagt ggctccttca atcgttgcgg ttctgtcagt   8400
tccaaacgta aaacggcttg tcccgcgtca tcggcggggg tcataacgtg actcccttaa   8460
ttctccgctc atgatcagat tgtcgtttcc cgccttcagt ttaaactatc agtgtttgac   8520
aggatatatt ggcgggtaaa cctaagagaa aagacgttt attagaataa tcggatattt   8580
aaaagggcgt gaaaaggttt atccgttcgt ccatttgtat gtgcatgcca accacagggt   8640
tccccagatc tggcgccggc cagcgagacg agcaagattg gccgccgccc gaaacgatcc   8700
gacagcgcgc ccagcacagg tgcgcaggca aattgcacca acgcatacag cgccagcaga   8760
atgccatagt gggcggtgac gtcgttcgag tgaaccagat cgcgcaggag gcccggcagc   8820
accggcataa tcaggccgat gccgacagcg tcgagcgcga cagtgctcag aattacgatc   8880
aggggtatgt tgggtttcac gtctggcctc cggagactgt catacgcgta aaaaggccgc   8940
gttgctggcg ttttttccata ggctccgccc cctgacgag catcacaaaa atcgacgctc   9000
aagtcagagg tggcgaaacc cgacaggact ataaagatac caggcgtttc ccctggaag    9060
ctccctcgtg cgctctcctg ttccgaccct gccgcttacc ggatacctgt ccgcctttct   9120
ccttcggga agcgtggcgc tttctctag ctcacgctgt aggtatctca gttcggtgta   9180
ggtcgttcgc tccaagctgg gctgtgtgca cgaaccccc gttcagcccg accgctgcgc   9240
cttatccggt aactatcgtc ttgagtccaa cccggtaaga cacgacttat cgccactggc   9300
agcagccact ggtaacagga ttagcagagc gaggtatgta ggcggtgcta cagagttctt   9360
gaagtggtgg cctaactacg gctacactag aaggacagta tttggtatct gcgctctgct   9420
gaagccagtt accttcggaa aaagagttgg tagctcttga tccggcaaac aaaccaccgc   9480
tggtagcggt ggtttttttg tttgcaagca gcagattacg cgcagaaaaa aaggatctca   9540
agaagatcct ttgatctttt ctacgggtc tgacgctcag tggaacgaaa actcacgtta   9600
agggattttg gtcatgagat tatcaaaaag gatcttcacc tagatccttt taaattaaaa   9660
atgaagtttt aaatcaatct aaagtatata tgagtaaact tggtctgcag ttgccatgtt   9720
ttacggcagt gagagcagag atagcgctga tgtccggcgg tgcttttgcc gttacgcacc   9780
accccgtcag tagctgaaca ggagggacag ctgatagaca cagaagccac tggagcacct   9840
caaaaacacc atcatacact aaatcagtaa gttggcagca tcacccataa ttgtggtttc   9900
aaaatcggct ccgtcgatac tatgttatac gccaactttg aaaacaactt tgaaaaagct   9960
gttttctggt atttaaggtt ttagaatgca aggaacagtg aattggagtt cgtcttgtta  10020
taattagctt cttggggtat cttttaaatac tgtagaaaag aggaaggaaa taattcaggt  10080
ctaaaatgag aatatcaccg gaattgaaaa aactgatcga aaaataccgc tgcgtaaaag  10140
atacggaagg aatgtctcct gctaaggtat ataagctggt gggagaaaat gaaaacctat  10200
atttaaaaat gacggacagc cggtataaag ggaccaccta tgatgtggaa cgggaaaagg  10260
acatgatgct atggctggaa ggaaaagctgc ctgttccaaa ggtcctgcac tttgaaccgc  10320
atgatgctg gagcaatctg ctcatgagtg aggccgatgg cgtcctttgc tcggaagagt  10380
atgaagatga caaagccct gaaaagatta tcgagctgta tgcggagtgc atcaggctct  10440
ttcactccat cgacatatcg gattgtccct atacgaatag cttagacagc cgcttagccg  10500
aattggatta cttactgaat aacgatctgg ccgatgtgga ttgcgaaaac tgggaagaag  10560
acactccatt taaagatccg cgcgagctgt atgattttt aaagacgaa aagcccgaag  10620
aggaacttgt ctttttccac ggcgacctgg gagacagcaa catctttgtg aaagatggca  10680
aagtaagtgg ctttattgat cttgggagaa gcggcagggc ggacaagtgg tatgacattg  10740
ccttctgcgt ccggtcgatc agggaggata tcggggaaga acagtatgtc gagctatttt  10800
ttgacttact ggggatcaag cctgattggg agaaaataaa atatttatatt ttactggatg  10860
aattgtttta gtacctagat gtggcgcaac gatgccggcg acaagcagga gcgcaccgac  10920
ttcttccgca tcaagtgttt tggctctcag gccgaggccc acggcaagta tttgggcaag  10980
gggtcgctgg tattcgtgca gggcaagatt cggaatacca agtacgagaa ggacggccag  11040
acggtctacg gaaccgactt cattgccgat aaggtggatt atctgacac caaggccacca  11100
ggcgggtcaa atcaggaata agggcacatt gccccgcgt gagtcgggcc aatcccgcaa  11160
ggagggtgaa tgaatcggac gtttgaccgg aaggcataca ggcaagaact gatcgacgcg  11220
gggttttccg ccgaggatgc cgaaaccatc gcaagccgca ccgtcatgcg tgcgcccgc   11280
gaaaccttcc agtccgtcgg ctcgatggtc cagcaagcta cggccaagat cgagcgcgac  11340
agcgtgcaac tggctccccc tgccctgccc cgcccatcgg ccgccgtgga gcgttcgcgt  11400
cgtctcgaac aggaggcggg aggtttggcg aagtcgatga ccatcgatgg gcgaggaact  11460
atgacgacca agaagcgaaa aaccgccggc gaggacctgg caaaacaggt cagcgaggcc  11520
aagcaggccg cgttgctgaa acacacgaag cagcagatca aggaaatgca gctttccttg  11580
ttcgatattg cgccgtggcc ggacacgatg cgagcgatgc caaacgacac ggcccgctct  11640
gccctgttca ccacgcgcaa caagaaaatc ccgcgcgagg cgctgcaaaa caaggtcatt  11700
ttccacgtca acaaggacgt gaagatcacc tacaccggcg tcgagctgcg ggccgacgat  11760
```

-continued

```
gacgaactgg tgtggcagca ggtgttggag tacgcgaagc gcaccccctat cggcgagccg    11820
atcaccttca cgttctacga gctttgccag gacctgggct ggtcgatcaa tggccggtat    11880
tacacgaagg ccgaggaatg cctgtcgcgc ctacaggcga cggcgatggg cttcacgtcc    11940
gaccgcgttg ggcacctgga atcggtgtcg ctgctgcacc gcttccgcgt cctggaccgt    12000
ggcaagaaaa cgtcccgttg ccaggtcctg atcgacgagg aaatcgtcgt gctgtttgct    12060
ggcgaccact acacgaaatt catatgggag aagtaccgca agctgtcgcc gacggcccga    12120
cggatgttcg actatttcag ctcgcaccgg gagccgtacc cgctcaagct ggaaaccttc    12180
cgcctcatgt gcggatcgga ttccaccgc gtgaagaagt ggcgcgagca ggtcggcgaa    12240
gcctgcgaag agttgcgagg cagcggcctg gtggaacacg cctgggtcaa tgatgacctg    12300
gtgcattgca aacgctaggg cctttgtggg tcagttccgg ctgggggttc agcagcagc    12360
gctttactgg catttcagga acaagcgggc actgctcgac gcacttgctt cgctcagtat    12420
cgctcgggac gcacgcgcg ctctacgaac tgccgataaa cagaggatta aaattgacaa    12480
ttcaatggca aggactgcca gcgctgccat ttttggggtg aggccgttcg cggccgaggg    12540
gcgcagcccc tgggggatg ggaggccgc gttagcgggc cgggagggtt cgagaagggg    12600
gggcaccccc cttcggcgtg cgcggtcacg cgcacagggc gcagccctgg ttaaaaacaa    12660
ggtttataaa tattggttta aaagcaggtt aaaagacagg ttagcggtgg ccgaaaaacg    12720
ggcggaaacc cttgcaaatg ctggattttc tgcctgtgga cagcccctca aatgtcaata    12780
ggtgcgcccc tcatctgtca gcactctgcc cctcaagtgt caaggatcgc gcccctcatc    12840
tgtcagtagt cgcgcccctc aagtgtcaat accgcagggc acttatcccc aggcttgtcc    12900
acatcatctg tgggaaactc gcgtaaaatc aggcgttttc gccgatttgc gaggctggcc    12960
agctccacgt cgccggccga aatcgagcct gcccctcatc tgtcaacgcc gcgccggtg    13020
agtcggcccc tcaagtgtca agtccgccc ctcatctgtc agtgagggcc aagttttccg    13080
cgaggtatcc acaacgccgg cggccgcggt gtctcgcaca cggcttcgac ggcgtttctg    13140
gcgcgtttgc agggccatag acggccgcca gcccagcggc gagggcaacc agccccggtga    13200
gcgtcgcaaa ggcgctcggt cttgccttgc tcgtcgagat ctgggtcga tcagccgggg    13260
atgcatcagg ccgacagtcg gaacttcggg tccccgacct gtaccattcg gtgagcaatg    13320
gatagggagag ttgatatcgt caacgttcac ttctaaagaa atagcgccac tcagcttcct    13380
cagcggcttt atccagcgat ttcctattat gtcggcatag ttctcaagat cgacagcctg    13440
tcacggttaa gcgagaaatg aataagaagg ctgataattc ggatctctgc gagggagatg    13500
atatttgatc acaggcagca agctctgtc atcgttacaa tcaacatgct accctccgcg    13560
agatcatccg tgtttcaaac ccggcagctt agttgccgtt cttccgaata gcatcggtaa    13620
catgagcaaa gtctgccgcc ttacaacggc tctcccgctg acgccgtccc ggactgatgg    13680
gctgcctgta tcgagtggtg attttgtgcc gagctgccgg tcggggagct gttggctggc    13740
tggtggcagg atatattgtg gtgtaaacaa attgacgctt agacaactta ataacacatt    13800
gcggacgttt ttaatgtact gggttggttt ttctttttcac cagtgagacg ggcaacagct    13860
gattgccctt caccgcctgg ccctgagaga gttgcagcaa gcggtccacg ctggtttgcc    13920
ccagcaggcg aaaatcctgt ttgatgctgg ttccgaaatc ggcaaaatcc cttataaatc    13980
aaaagaatag cccgagatag ggttgagtgt tgttccagtt tggaacaaga gtccactatt    14040
aaagaacgtg gactccaacg tcaaagggcg aaaaaccgtc tatcagggcg atggcccact    14100
acgtgaacca tcacccaaat caagtttttt ggggtcgagg tgccgtaaag cactaaatcg    14160
gaaccctaaa gggagccccc gatttagagc ttgacgggga aagccggcga acgtggcgag    14220
aaaggaaggg aagaaagcga aaggagcggg cgccattcag gctgcgcaac tgttgggaag    14280
gg                                                                   14282
```

```
SEQ ID NO: 15            moltype = AA  length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 15
HHHHHHGS                                                               8

SEQ ID NO: 16            moltype = AA  length = 370
FEATURE                  Location/Qualifiers
source                   1..370
                         mol_type = protein
                         organism = Clostridium perfringens
SEQUENCE: 16
WDGKIDGTGT HAMIVTQGVS ILENDMSKNE PESVRKNLEI LKDNMHELQL GSTYPDYDKN      60
AYDLYQDHFW DPDTNNNFSK DNSWYLAYSI PDTGESQIRK FSALARYEWQ RGNYKQATFY     120
LGEAMHYFGD IDTPYHPANV TAVDSAGHVK FETFAEERKE QYKINTVGCK TNEDFYADIL     180
KNKDFNAWSK EYARGFAKTG KSIYYSHASM SHSWDDWDYA AKVTLANSQK GTAGYIYRFL     240
HDVSEGNDPS VGNNVKELVA YISTSGEKDA GTDDYMYFGI KTKDGKTQEW EMDNPGNDFM     300
AGSKDTYTFK LKDENLKIDD IQNMWIRKRK YTAFPDAYKP ENIKVIANGK VVVDKDINEW     360
ISGNSTYNIK                                                           370

SEQ ID NO: 17            moltype = AA  length = 322
FEATURE                  Location/Qualifiers
source                   1..322
                         mol_type = protein
                         organism = Clostridium perfringens
SEQUENCE: 17
MKRLKIISIT LVLTSVISTS LFSTQTQVFA SELNDINKIE LKNLSGEIIK ENGKEAIKYT      60
SSDTASHKGW KATLSGTFIE DPHSDKKTAL LNLEGFIPSD KQIFGSKYYG KMKWPETYRI     120
NVKSADVNNN IKIANSIPKN TIDKKDVSNS IGYSIGGNIS VEGKTAGAGI NASYNVQNTI     180
```

```
SYEQPDFRTI QRKDDANLAS WDIKFVETKD GYNIDSYHAI YGNQLFMKSR LYNNGDKNFT   240
DDRDLSTLIS GGFSPNMALA LTAPKNAKES VIIVEYQRFD NDYILNWETT QWRGTNKLSS   300
TSEYNEFMFK INWQDHKIEY YL                                           322
```